United States Patent
Wang et al.

(10) Patent No.: US 11,957,764 B2
(45) Date of Patent: Apr. 16, 2024

(54) PROTEIN-TYPE NANOPARTICLES, PREPARATION METHODS, AND APPLICATION THEREOF

(71) Applicant: SOUTH CHINA UNIVERSITY OF TECHNOLOGY, Guangdong (CN)

(72) Inventors: Jun Wang, Guangzhou (CN); Zhiting Cao, Guangzhou (CN); Song Shen, Guangzhou (CN); Qianni Ye, Guangzhou (CN); Xiaojiao Du, Guangzhou (CN); Xianzhu Yang, Guangzhou (CN); Youyong Yuan, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 18/161,036

(22) Filed: Jan. 27, 2023

(65) Prior Publication Data

US 2023/0173100 A1    Jun. 8, 2023

Related U.S. Application Data

(63) Continuation of application No. PCT/CN2020/122361, filed on Oct. 21, 2020.

(30) Foreign Application Priority Data

Aug. 4, 2020    (CN) .......................... 202010774475.1

(51) Int. Cl.
*A61K 39/395*    (2006.01)
*A61K 47/62*    (2017.01)
*A61K 47/69*    (2017.01)

(52) U.S. Cl.
CPC .......... *A61K 47/6937* (2017.08); *A61K 47/62* (2017.08)

(58) Field of Classification Search
None
See application file for complete search history.

(56) References Cited

U.S. PATENT DOCUMENTS

2014/0377334 A1* 12/2014 Irvine .................. A61K 9/1271
424/490
2016/0090415 A1   3/2016 Marquette et al.
2018/0021440 A1* 1/2018 Yu ..................... A61K 47/6851
424/178.1

FOREIGN PATENT DOCUMENTS

| CN | 101658676 A | 3/2010 |
| CN | 106633015 A | 5/2017 |
| CN | 106729623 A | 5/2017 |
| CN | 109954145 A | 7/2019 |
| CN | 110669137 A | 1/2020 |
| CN | 111263632 A | 6/2020 |
| CN | 112336873 A | 2/2021 |

OTHER PUBLICATIONS

International Search Report in PCT/CN2020/122361 dated May 7, 2021, 10 pages.
Written Opinion in PCT/CN2020/122361 dated May 7, 2021, 14 pages.
Yao, Yong-Chao et al., A Specific Drug Targeting System Based on Polyhydroxyalkanoate Granule Binding Protein PhaP Fused with Targeted Cell Ligands, Biomaterials, 29: 4823-4830, 2008.
Driton Vllasaliu et al., Fc-mediated Transport of Nanoparticles Across Airway Epithelial Cell Layers, Journal of Controlled Release, 158: 479-486, 2012.
Wang, Jianzhu et al., Preparation of Bovine Serum Albumin-Modified PLGA Nanoparticles Loaded with Naringenin, Chinese Traditional Patent Medicine, 41(11): 2566-2571, 2019.
First Office Action in Chinese Application No. 202010774475.1 dated Dec. 16, 2021, 13 pages.
The Second Office Action in Chinese Application No. 202010774475.1 dated Mar. 9, 2022, 7 pages.
Decision to Grant a Patent in Chinese Application No. 202010774475.1 dated Mar. 23, 2022, 4 pages.
Masumi Lijima et al., Nanocapsules Incorporating IgG Fc-binding Domain Derived from *Staphylococcus aureus* Protein A for Displaying IgGs on Immunosensor Chips, Biomaterials, 32(6): 1455-1464, 2011.
Alyssa K. Kosmides et al., Dual Targeting Nanoparticle Stimulates the Immune System To Inhibit Tumor Growth, Acs Nano, 2017, 13 pages.

* cited by examiner

*Primary Examiner* — Yunsoo Kim
(74) *Attorney, Agent, or Firm* — METIS IP LLC

(57) ABSTRACT

The disclosure relates to a protein-type nanoparticle for multi-specific antibody delivery, a preparation method, and its application. The protein-type nanoparticle includes a polyester and a protein with a hydrophobic domain, and the hydrophobic domain of the protein is bound with the polyester through hydrophobic interactions. The protein is at least one of albumin, globulin and cell wall protein. The protein-type nanoparticle of the present disclosure has excellent stability and biocompatibility. The protein-type nanoparticle is used to prepare a multi-specific antibody delivery platform (αFc-NP) by binding anti-IgG-Fc antibody or anti-IgG-Fc antibody fragment, which can stably, quickly and easily bind to multiple specific antibodies through antigen-antibody interaction and enhance the therapeutic effect of specific antibodies.

10 Claims, 19 Drawing Sheets

|  | Size(nm) | PDI |
|---|---|---|
| $NP_{HSA/PLLA-COOR-1100K}$ | 167.5±3.5 | 0.159 |
| $NP_{BSA/PLLA-COOR-1100K}$ | 146.2±2.3 | 0.132 |
| $NP_{MSA/PLLA-COOR-1100K}$ | 177.6±3.4 | 0.207 |

|  | Size (nm) | PDI |
|---|---|---|
| NP$_{HSA/PLGA(LA/GA=95/5)}$ | 74.8 ± 0.4 | 0.193 |
| NP$_{HSA/PLGA(LA/GA=85/15)}$ | 76.0 ± 0.7 | 0.218 |
| NP$_{HSA/PLGA(LA/GA=75/25)}$ | 109.5 ± 1.1 | 0.268 |
| NP$_{HSA/PLGA(LA/GA=50/50)}$ | 116.8 ± 1.8 | 0.209 |

|  | Size(nm) | PDI |
|---|---|---|
| $NP_{HSA/PDLLA-OH-460K}$ | 140.8 ± 3.5 | 0.164 |
| $NP_{HSA/PDLLA-COOH-480K}$ | 144.1 ± 1.4 | 0.119 |

| | Size (nm) | PDI |
|---|---|---|
| NP$_{HSA/PLLA-COOR-7.2K}$ | 115.8 ± 1.7 | 0.136 |
| NP$_{HSA/PLLA-COOR-36K}$ | 102.9 ± 0.7 | 0.100 |
| NP$_{HSA/PLLA-COOR-137K}$ | 108.5 ± 1.5 | 0.076 |
| NP$_{HSA/PLLA-COOR-240K}$ | 87.4 ± 1.4 | 0.106 |
| NP$_{HSA/PLLA-COOR-600K}$ | 119.3 ± 1.1 | 0.115 |

|  | Size(nm) | PDI |
|---|---|---|
| $NP_{HSA/PEG5K-PLGA16k}$ | 137.2±1.4 | 0.224 |
| $NP_{HSA/PEG5K-PCL11.8k}$ | 134.1±2.7 | 0.273 |
| $NP_{HSA/PEG5K-PLA16k}$ | 131.6±1.5 | 0.245 |

NP<sub>HSA/PLLA240k-COOR</sub> (0.3/1)

NP<sub>HSA/PLLA240k-COOR</sub> (25/1)

NP<sub>HSA/PLLA240k-COOR</sub> (10/1)

NP<sub>HSA/PLLA240k-COOR</sub> (5/1)

PROTEIN-TYPE NANOPARTICLES, PREPARATION METHODS, AND APPLICATION THEREOF

CROSS-REFERENCE TO RELATED APPLICATIONS

This application is a Continuation of International Application No. PCT/CN 2020/122361, filed on Oct. 21, 2020, which claims priority to Chinese application 202010774475.1, filed on Aug. 4, 2020, the entire contents of which are hereby incorporated by reference.

TECHNICAL FIELD

The present application relates to the field of medical technology, in particular to a protein-type nanoparticle for multi-specific antibody delivery, preparation method, and application thereof.

BACKGROUND

Monoclonal antibodies (mAbs) are the largest class of therapeutic proteins, which may be used for a variety of diseases, such as tumors, inflammation, and autoimmune diseases. Most therapeutic antibodies achieve therapeutic purposes by blocking receptors or ligands, thereby reducing the activity of certain signaling pathways. Since the first monoclonal antibody used to block CD3 in the treatment of renal transplant rejection was approved by the Food and Drug Administration (FDA) in 1986, after more than 30 years of rapid development, monoclonal antibody drugs, including therapeutic antibodies and antibody derivatives (including antigen-binding fragment Fab, Fc fusion protein, etc.), has become the fastest-growing segment of global biopharmaceuticals, and several "super blockbuster drugs" with annual sales exceeding 5 billion dollars have been born. In 2006, the US FDA approved the monoclonal antibody ranibizumab of the anti-vascular endothelial growth factor (anti-VEGF) as a new drug for age-related macular degeneration (AMD)) patients, which improves the vision of up to 40% of patients. Monoclonal antibody drugs have good synergistic properties and a high success rate in clinical applications. More than 550 kinds of antibodies have been developed clinically, and it is predicted that about 70 kinds of monoclonal antibodies will enter the market to treat various diseases by 2020. In 2018, the global drug sales of biotech drugs reached 261.8 billion dollars, and the scale of monoclonal antibody drugs reached 119.3 billion dollars. Antibody drugs have become the largest category of biotech drugs in terms of research and development scale and sale scale, and the development and optimization of antibody drugs have become an inevitable trend in the development of global medicine.

Although antibody drugs have good specificity and high efficiency, the clinical application of antibody drugs is still limited. First, the half-life of the antibody after entering the blood circulation is very short, even only a few h, and the frequency of administration is high during treatment, which not only leads to strong side effects, but also results in high treatment costs and poor compliance. In addition, antibodies have large molecular weights, poor structural stability, and poor tissue permeability, thus it is a challenge to effectively deliver antibodies to target tissues and cells. At the beginning of the 21st century, in order to solve the problem of high immunogenicity of heterogeneous therapeutic antibodies in the human body, Humanized Antibodies were developed and approved for marketing. Subsequently, in order to improve the clinical application rate of antibody drugs, various forms of antibody drugs were developed and approved. First, therapeutic or imaging antibody drug conjugates—binding chemotherapeutic drugs or radioisotopes to antibodies through the chemical bonds to increase the effect of antibody drugs, such as inotuzumab ozogamicin (anti-CD22), brentuximab vedotin (anti-CD30), 90Y-ibritumomab tiuxetan (anti-CD20), etc. Second, antibody fragment drugs, including Fab fragments and single-chain variable fragment scFv, which may increase the tissue penetration of antibody drugs, but the retention time in vivo is poor, such as ranibizumab (anti-VEGFA), brolucizumab (anti-VEGF), etc. Third, recombinant and chemically modified antibody drugs, including albumin fusion antibodies, Fc fusion protein antibodies, PEG-modified antibodies, etc., which may significantly reduce the immunogenicity of antibody drugs and prolong the half-life, such as Ozoralizumab (anti-TNF×HSA), alefacept (anti-CD20), certolizumab pegol (anti-TNF), etc. Fourth, bispecific antibodies, i.e., artificial antibody molecules with two different antigen-binding sites, such as blinatumomab (anti-CD3×CD19). Fifth, antibody drugs based on controlled release system, including PLGA microspheres, hydrogels, liposomes, etc., which may prolong the action time of antibodies in the body. For example, the PolyActive™ hydrogel system may release antibodies for up to 6 months.

In summary, the optimization of therapeutic antibodies needs to meet the following requirements: 1. reducing antibody aggregation and immunogenicity, increasing antibody stability, and prolonging half-life in vivo. 2. Increasing the active targeting of antibodies, including the active enrichment of target tissues. 3. Optimizing the production process and reducing production costs.

Therefore, it is desired to provide a simple, convenient, stable, and biocompatible antibody delivery system to achieve efficient delivery of therapeutic antibodies in vivo at low cost, especially multi-specific antibodies.

SUMMARY

Based on this, the purpose of the present disclosure is to provide a protein-type nanoparticle for the delivery of multi-specific antibody, which has excellent stability and biocompatibility. A multi-specific antibody delivery platform (αFc-NP) may be prepared by binding the protein-type nanoparticle and an anti-Fc antibody or an anti-Fc antibody fragment, which may stably, quickly, and easily bind to multiple specific antibodies through antigen-antibody interaction and have good application potential.

The specific technical scheme is a protein-type nanoparticle for delivery of a multi-specific antibody including a polyester and a protein with a hydrophobic domain, the hydrophobic domain of the protein being bound with the polyester through hydrophobic interaction. The protein is at least one of albumin, a globulin, and a cell wall protein.

Another purpose of the present disclosure is to provide a method for preparing the above-mentioned protein-type nanoparticle. The method may comprise:

(1) mixing the protein with water or an aqueous solution to obtain an aqueous phase; and mixing the polyester with an organic solvent to obtain an oil phase;

(2) preparing the water phase and the oil phase described in step (1) into an oil-in-water emulsion; and (3) separating and purifying the emulsion to obtain the protein-type nanoparticle.

Another purpose of the present disclosure is to provide an application of the above-mentioned protein-type nanoparticle in the preparation of a multi-specific antibody delivery platform.

Another purpose of the present disclosure is to provide a multi-specific antibody delivery platform, which is formed by binding the above-mentioned protein-type nanoparticle with an anti-Fc antibody or an anti-Fc antibody fragment through a chemical bond. The Fab domain of the anti-Fc antibody or anti-Fc antibody fragment may be non-covalently bound with the Fc domain of the delivered specific antibody. The delivered specific antibody has the same species as the Fc segment recognized by the anti-Fc antibody fragment.

Another purpose of the present disclosure is to provide a method for preparing the above-mentioned multi-specific antibody delivery platform. The method may comprise:

(A) oxidizing the anti-Fc antibody with an oxidant to obtain an anti-Fc antibody containing an aldehyde group; and (B) reacting the anti-Fc antibody containing aldehyde group obtained in step (A) with the protein-type nanoparticle to obtain a product, and then reducing the obtained product with a reducing agent.

Another purpose of the present disclosure is to provide an application of the above-mentioned protein-type nanoparticle or multi-specific antibody delivery platform in the delivery of multi-specific antibody or in the preparation of a multi-specific antibody delivery system.

Another purpose of the present disclosure is to provide a multi-specific antibody delivery system. The multi-specific antibody delivery system may include the above-mentioned multi-specific antibody delivery platform and the specific antibody.

Another purpose of the present disclosure is to provide an application of the above-mentioned protein-type nanoparticle or multi-specific antibody delivery platform or multi-specific antibody delivery system in the preparation of immunotherapeutic drugs.

Compared with the prior art, the present disclosure has the following beneficial effects. The protein-type nanoparticle for multi-specific antibody delivery is prepared by selecting the polyester and the specific protein with the hydrophobic domain, and the hydrophobic polyester binds with the hydrophobic domain of the protein through mutual hydrophobic interaction, which has excellent stability and remains integrityduring the long cycle, thereby maintaining the multivalent state of the multi-specific antibody on the surface of the protein-type nanoparticle. The surface of the protein has a hydrophilic domain, which is distributed with a large number of hydrophilic groups (such as amino, carboxyl, and thiol), which can be bonded with anti-IgG-Fc antibody to obtain a multi-specific antibody delivery platform (αFc-NP), and then αFc-NP can quickly, stably, and specifically bind a variety of specific antibodies and enhance the therapeutic effect of specific antibodies. In addition, the hydrophilic domain on the surface of the protein is also conducive to the dispersion of αFc-NP in vivo.

The αFc-NP prepared from the protein-type nanoparticle of the present disclosure is assembled from high-molecular polyester approved by the FDA and albumin from natural sources, which has excellent biocompatibility.

The αFc-NP of the present disclosure is conducive to the outward exposure of the Fab segment of the specific antibody, so that the function of the antibody may be preserved to the greatest extent.

In the present disclosure, the nanoparticle of double-layer antibodies is formed by strongly binding αFc-NP with multi-specific antibodies, which has the characteristics of multivalence, multi-specificity, and multifunctionality. The nanoparticle of double-layer antibodies may quickly combine different therapeutic antibodies to adapt to the strategy of personalized treatment plan under the current clinical precision treatment, which has great potential for clinical application.

BRIEF DESCRIPTION OF THE DRAWINGS

The present disclosure is further described in terms of exemplary embodiments. These exemplary embodiments are described in detail with reference to the drawings. These embodiments are not limited, in these embodiments, the same numbers denote the same structures, wherein.

DETAILED DESCRIPTION

Figure 1:
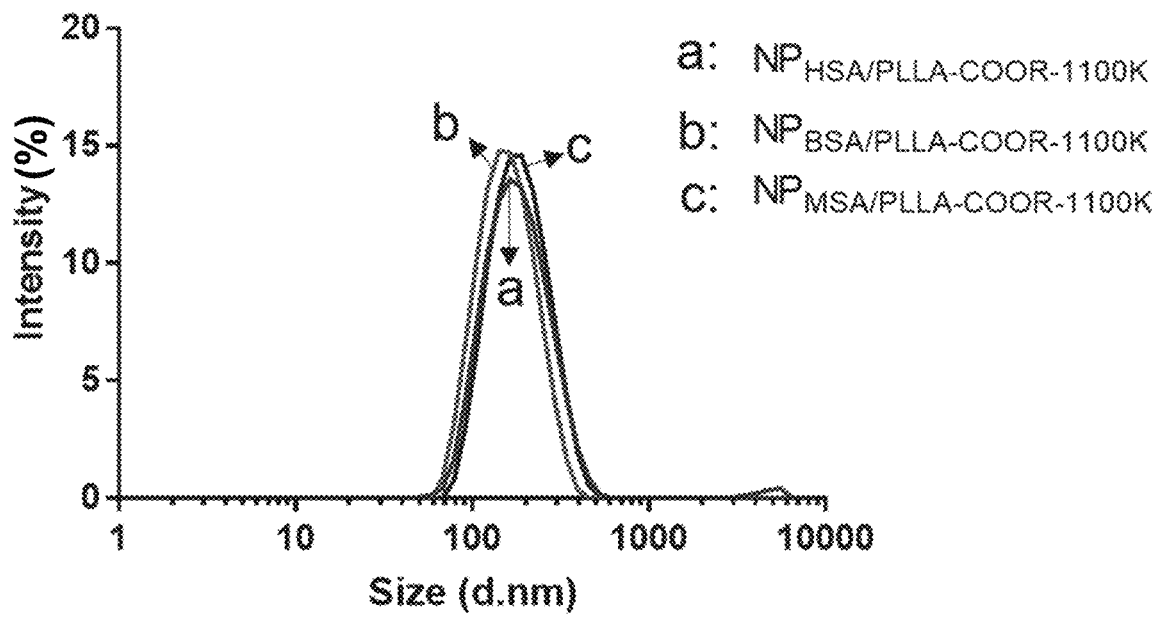
FIG. 1 is a diagram illustrating the particle size of particles of albumin with different species and polyester according to some embodiments of the present disclosure.
Figure 2:
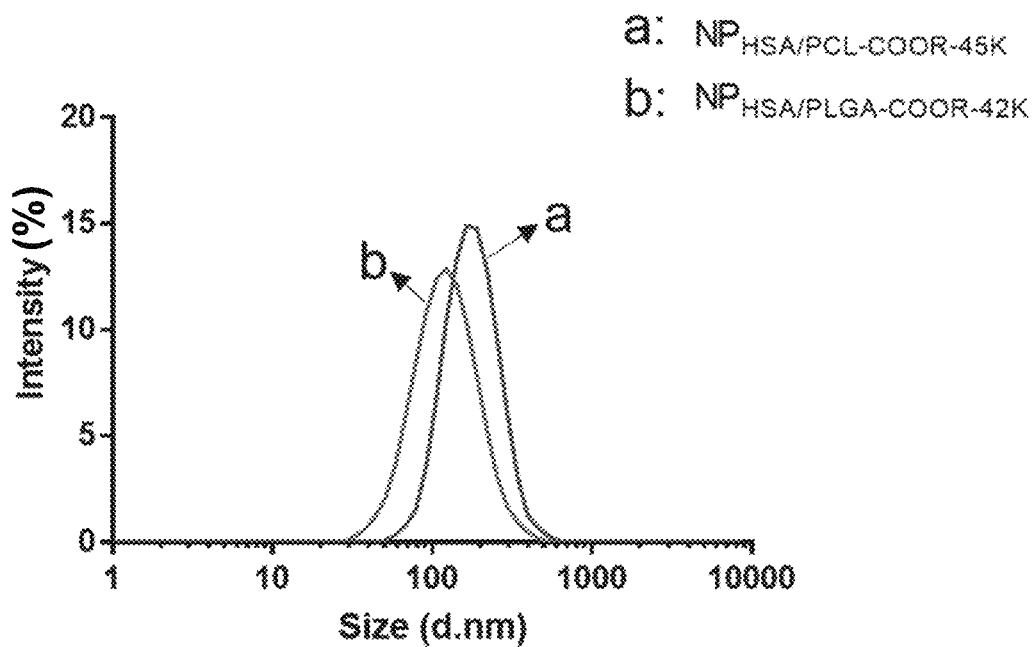
FIG. 2 is a diagram illustrating the particle size of particles of human serum albumin and aliphatic polyesters with different kinds according to some embodiments of the present disclosure.
Figure 3:
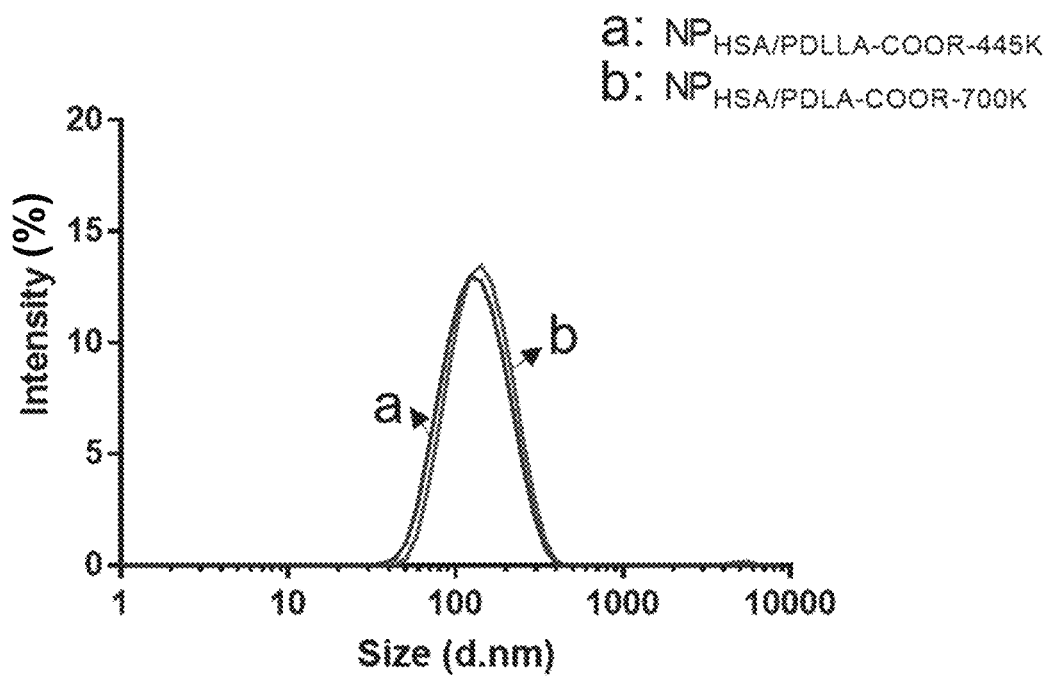
FIG. 3 is a diagram illustrating the particle size of particles of human serum albumin and polylactic acid with different optical activity according to some embodiments of the present disclosure.
Figure 4:
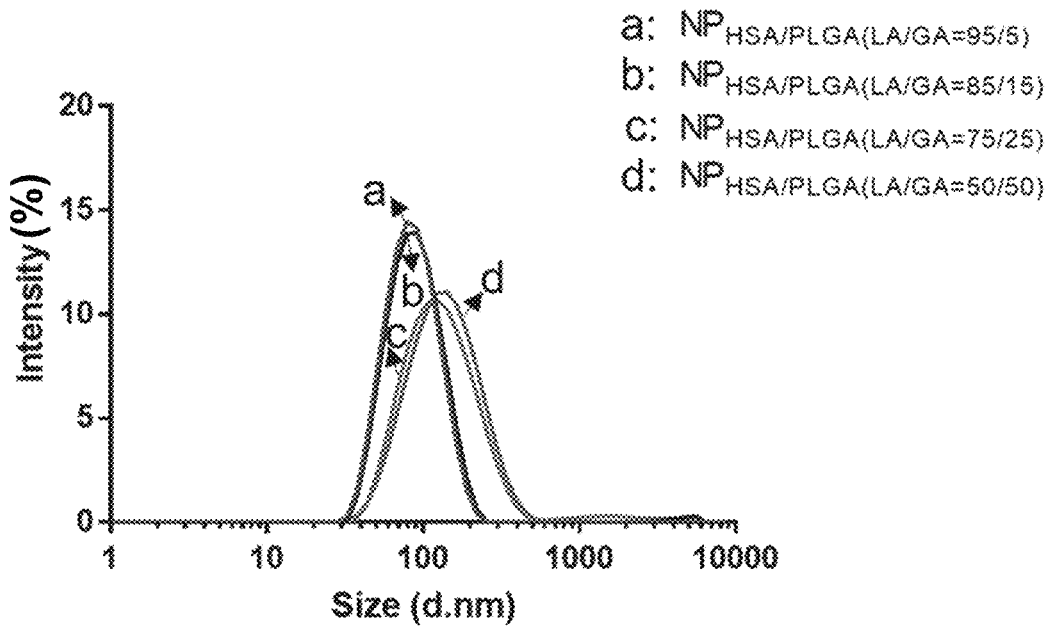
FIG. 4 is a diagram illustrating the particle size of particles of human serum albumin and poly(glycolide-co-lactide) with different LA/GA ratios according to some embodiments of the present disclosure.
Figure 5:
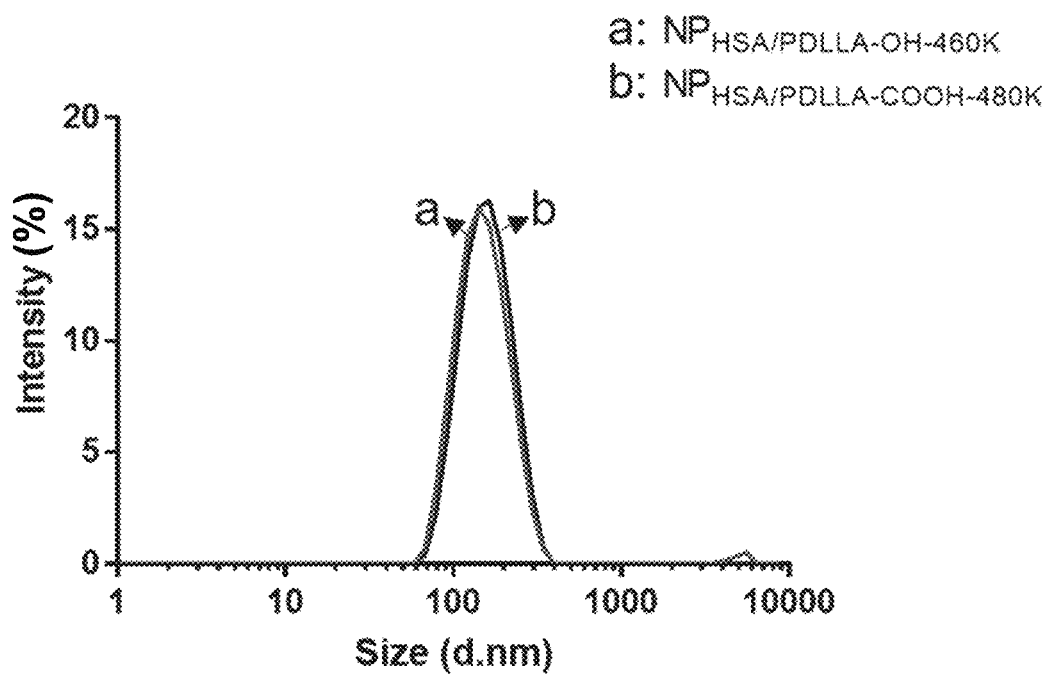
FIG. 5 is a diagram illustrating the particle size of particles of human serum albumin and L-polylactic acid modified by different terminal groups according to some embodiments of the present disclosure.
Figure 6:
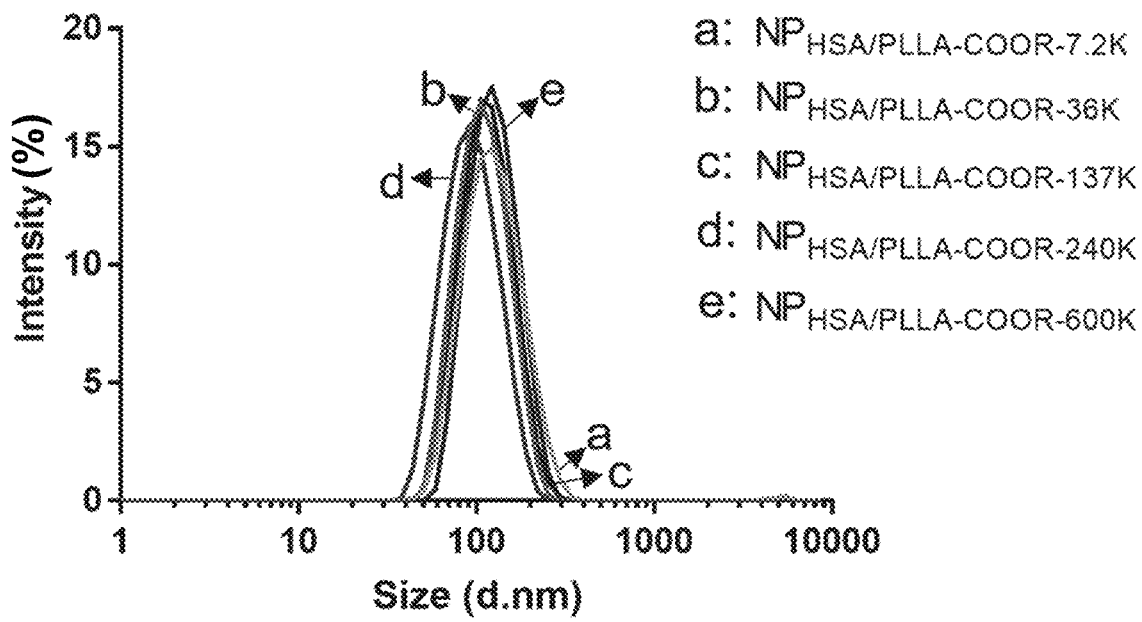
FIG. 6 is a diagram illustrating the particle size of particles of human serum albumin and L-polylactic acid with different molecular weights according to some embodiments of the present disclosure.
Figure 7:
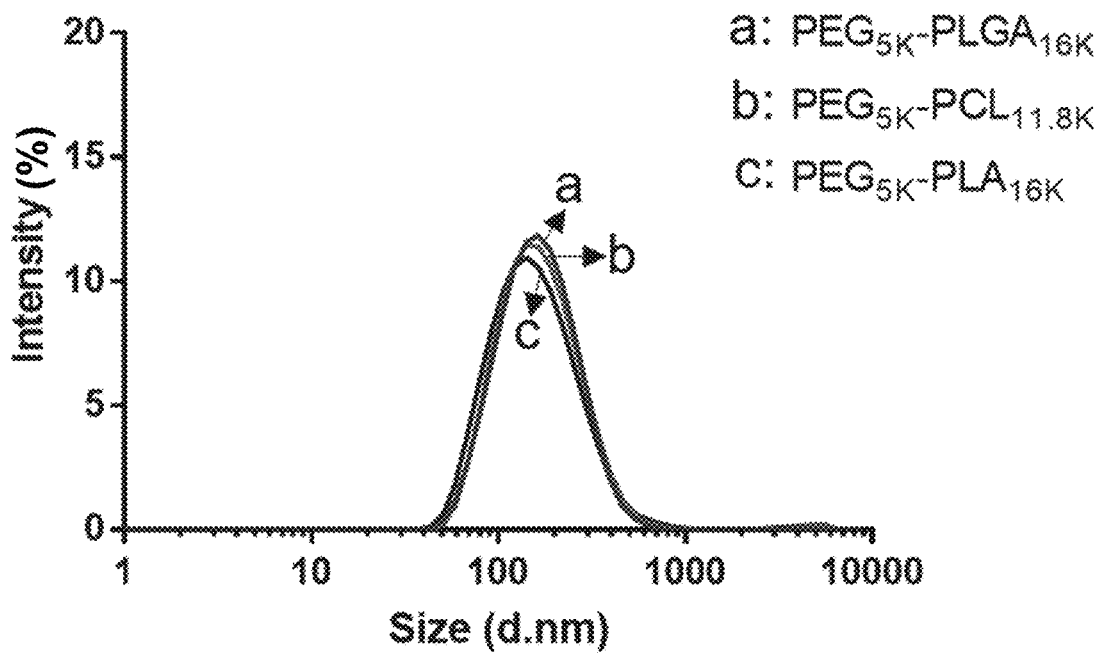
FIG. 7 is a diagram illustrating the particle size of particles of human serum albumin and the polyethylene glycol-modified aliphatic polyester according to some embodiments of the present disclosure.

In order to more clearly explain the technical scheme of the embodiment of this description, a brief description of the accompanying drawings required for the embodiment description is given below. Obviously, the accompanying drawings below are only some examples or embodiments of this description, and it is possible for ordinary technicians skilled in the art to apply this description to other similar scenarios according to these accompanying drawings without creative effort. Unless otherwise apparent from context or otherwise indicated, like reference numerals in the figures represent like structures or operations.

As shown in this description and claims, the words "one", "a", "a kind" and/or "the" are not special singular but may include the plural unless the context expressly suggests otherwise. Generally speaking, the terms "comprise", "comprises", "comprising", "include", "includes", and "including" only indicate that steps, elements and/or substances that have been clearly identified are included, and these steps, elements and/or substances do not constitute an exclusive list, and methods or platforms may also include other steps, elements and/or substances.

The experimental methods without specific conditions indicated in the following embodiments of the present disclosure are generally in accordance with conventional conditions, or in accordance with the conditions suggested by the manufacturer. Various commonly used chemical reagents used in the embodiments are all commercially available products. Unless otherwise defined, all technical and scientific terms used in this disclosure have the same meaning as commonly understood by one of ordinary skill in the technical field of this disclosure. The terms used in the description of the present disclosure are only used to describe specific embodiments, and are not used to limit the present disclosure.

The terms "include", "includes", "including", "have", "has", "having", and any variations thereof in the present disclosure are intended to cover a non-exclusive inclusion. For example, a process, method, device, product or equipment that includes a series of steps is not limited to the listed steps or modules, but also optionally includes steps that are not listed, or also optionally includes other steps inherent to these processes, a method, product, or equipment.

The "plurality" mentioned in the present disclosure means two or more. "And/or" describes the association relationship of associated objects, indicating that there may be three types of relationships, for example, A and/or B may indicate that A exists alone, A and B exist simultaneously, and B exists independently. The character "/" generally indicates that the contextual objects are an "or" relationship.

This embodiment provides a protein-type nanoparticle for multi-specific antibody delivery. The protein-type nanoparticle may include a polyester and a protein with a hydrophobic domain, and the hydrophobic domain of the protein may bind to the polyester through manual hydrophobic interaction. The protein may be at least one of albumin, globulin, and cell wall protein.

The protein may have the same specie as the recipient of the delivered specific antibody. The recipient of the specific antibody refers to the treatment object who receives the specific antibody. For example, if the recipient of the specific antibody is a person, the protein may be human serum albumin. For another example, if the recipient of the specific antibody is a mouse, the protein may be mouse serum albumin.

In some of the embodiments, the albumin may be serum albumin or ovalbumin (ova). Serum albumin is the most abundant protein in plasma. Albumin from natural sources has low immunogenicity and excellent histocompatibility, and albumin-binding protein is highly expressed in many tumors and neovascular endothelial cells of tumors. Therefore, albumin carriers may mediate drug targeting to tumors. From a chemical point of view, the hydrophilic region on the surface of albumin exposes a large number of modifiable groups, such as amino, carboxyl, and sulfhydryl groups, while the surface has multiple hydrophobic domains (hydrophobic binding sites), which can be assembled with hydrophobic polyester. In particular, the study found that the hydrophilic region of albumin is bound to the anti-Fc antibody or anti-Fc antibody fragment through chemical bond to obtain a specific antibody delivery platform αFc-NP, which can quickly and stably bind specific antibody through intermolecular interactions.

In some embodiments, the albumin may be serum albumin. In some embodiments, the serum albumin may be bovine serum albumin, mouse serum albumin, or human serum albumin. In actual clinical use, the human serum albumin is used for human treatment, that is, the protein has the same species as the treatment object of the delivered antibody, so as to avoid rejection of the recipient.

In some embodiments, the globulin may be immunoglobulin G (IgG).

In some embodiments, the cell wall protein may be protein A and protein G.

In some embodiments, the polyester may be aliphatic polyester or polyethylene glycol-modified aliphatic polyester. The aliphatic polyester may be at least one of polylactic acid (PLA), polyglycolide (PGA), poly(glycolide-co-lactide) (PLGA), and polycaprolactone (PCL).

In some embodiments, the polyethylene glycol-modified aliphatic polyester may be at least one of polyethylene glycol-modified polylactic acid (PEG-PLA), polyethylene glycol-modified polyglycolide (PEG-PGA), polyethylene glycol-modified poly(glycolide-co-lactide) (PEG-PLGA), and polyethylene glycol-modified polycaprolactone (PEG-PCL). In some of the embodiments, the polyethylene glycol-modified aliphatic polyester may be PEG-PLA, which has strong hydrophobicity and slow degradation rate.

In some embodiments, the aliphatic polyester may be polylactic acid. The polylactic acid may be L-polylactic acid (PLLA), D-polylactic acid (PDLA), or racemic polylactic acid (PDLLA). In some embodiments, the polylactic acid may be PLLA, which has strong hydrophobicity and slow degradation rate.

In some embodiments, the terminal group of the polylactic acid may be at least one of ester group, carboxyl group, and hydroxyl group. In some embodiments, the terminal group of polylactic acid may be ester group, which have stronger hydrophobicity.

In some of the embodiments, the molecular weight of the polyester may be within a range of 7,200 Daltons-1,100,000 Daltons.

In some embodiments, the aliphatic polyester may be PLLA, the terminal group of the PLLA may be an ester group, and the molecular weight of PLLA may be within a range of 7200 Daltons-1,100,000 Daltons. Preferably, the molecular weight of PLLA may be within a range of 100,000 Daltons-600,000 Daltons. Further preferably, the molecular weight of PLLA may be within a range of 100000 Daltons-240000 Daltons, at this time, the molecular weight and viscosity of the polyester are suitable, so that the particle of albumin and polyester has better stability.

In some embodiments, the polyester may be polyethylene glycol-modified aliphatic polyester. A molecular weight of the polyethylene glycol may be within a range of 4000 Daltons-6000 Daltons, the aliphatic polyester may be at least one of PLA, PLGA, and PCL, and the molecular weight of the aliphatic polyester may be within a range of 10,000 Daltons-18,000 Daltons.

Specifically, the initiators of the polylactic acid may be n-dodecyl alcohol, hydroxy acid, and diol respectively.

In some embodiments, the aliphatic polyester may be poly(glycolide-co-lactide), and a ratio of LA/GA may be within a range of 95/5-50/50. Specifically, the ratio of LA/GA may be 95/5, 85/15, 75/25, 50/50, or a range between any two specific ratios. For example, the ratio of LA/GA may be within a range of (95/5)-(85/15), (85/15)-(75/25), (75/25)-(50/50), (95/5)-(75/25), or (85/15)-(50/50). In some embodiments, the ratio of LA/GA may be within a range of (75±5)/25, the polymerization reaction of its large molecular weight is easy to control, and the solubility of the material is better.

In some embodiments, the weight ratio of the aliphatic polyester to the protein may be within a range of (1:0.1)-(1:30). Preferably, the weight ratio of the aliphatic polyester to the protein may be within a range of 1:(5-25). Further preferably, the weight ratio of the aliphatic polyester to the protein may be within a range of 1:(5-15). Futher preferably, the weight ratio of the aliphatic polyester to the protein may be within a range of 1:(8-12). Further preferably, the weight ratio of the aliphatic polyester to the protein may be within a range of 1:(9-11). The weight ratio of the aliphatic polyester to the protein may be also be 1:0.1, 1:0.3, 1:0.4, 1:0.5, 1:0.6, 1:0.8, 1:1,1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or a range between any two specific weight ratios mentioned above. Preferably, the protein-type nanoparticle prepared with the weight ratio of aliphatic polyester to protein of 1:(9-11) may the highest recovery rate and maximum protein utilization.

In some embodiments, the average particle size of the protein-type nanoparticle may be within a range of 74.8 nm-384.2 nm. Preferably, the particle size of the protein-type nanoparticle may be within a range of 100 nm-200 nm, and the surface of protein-type nanoparticles may bind specific antibody more efficiently.

This embodiment also provides a method for preparing the above-mentioned protein-type nanoparticle. The method may comprise the following steps.
(1) mixing the protein with water or an aqueous solution to obtain an aqueous phase; and mixing the polyester with an organic solvent to obtain an oil phase;
(2) preparing the water phase and the oil phase described in step (1) into an oil-in-water emulsion; and
(3) separating and purifying the emulsion to obtain protein-type nanoparticle.

In some embodiments, in step (1), the mass volume concentration of the protein in the aqueous phase may be within a range of 5 mg/mL-20 mg/m L.

In some embodiments, in step (1), the mass volume concentration of the polyester in the oil phase may be within a range of 1 mg/mL-10 mg/m L.

In some embodiments, in step (1), the organic solvent may be at least one of chloroform, dichloromethane, and ethyl acetate. More specifically, when the molecular weight of the polyester is small (7200 Daltons-137000 Daltons), the ethyl acetate system or the ethyl acetate-chloroform mixed system may be more fully emulsified, and the particle size of the prepared nanoparticle is smaller and easier to control. When the molecular weight of the polyester is large (137,000 Daltons-1,100,000 Daltons), the chloroform system or the dichloromethane-chloroform mixed system may make the polyester fully dissolved and easy to emulsify. The aqueous solution may be a sodium chloride aqueous solution.

In some embodiments, no additional stabilizers may be used during the preparation of the protein-type nanoparticle.

In some embodiments, in step (3), free protein and nanoparticle may be separated by at least one of centrifugation, tangential flow dialysis (dialysis under the action of tangential shear force through a tangential flow device), and exclusion chromatography (according to the molecular weight of nanoparticles and free protein).

In some embodiments, in step (2), the method for preparing the aqueous phase and the oil phase into an oil-in-water emulsion may include ultrasonic emulsification or high-pressure homogeneous emulsification.

This embodiment also provides an application of the above-mentioned protein-type nanoparticle in the preparation of a multi-specific antibody delivery platform.

This embodiment also provides the above-mentioned specific antibody delivery platform, which is formed by binding the above-mentioned protein-type nanoparticle to the anti-Fc antibody or anti-Fc antibody fragment through chemical bond. The delivered specific antibody has the same species as the Fc segment recognized by the anti-Fc antibody fragment, and the Fab domain of the anti-Fc antibody or the anti-Fc antibody fragment may be non-covalently bound with the Fc domain of the delivered specific antibody.

The anti-Fc antibody or anti-Fc antibody fragment of the multi-specific antibody delivery platform of the present disclosure may efficiently and conveniently specific binds (directionally, non-covalently) multiple specific antibodies through antibody-antigen specificit recognition, which may easily realize the "multivalency" and "multi-specificity" of antibodies and can retain the affinity (antigen binding ability) of specific antibodies to the greatest extent.

In some embodiments, the multi-specific antibody delivery platform may deliver at least two kinds of specific antibodies. For example, the multi-specific antibody delivery platform may deliver two specific antibodies. For another example, the multi-specific antibody delivery platform may deliver three specific antibodies. For another example, the multi-specific antibody delivery platform may deliver five specific antibodies.

The multi-specific antibody delivery platform of the present disclosure has versatility, does not destroy the structure of specific antibody, and overcomes the defects that the traditional chemical bonding and immobilization method destroys the structure of antibody drugs, blocks its antibody recognition region, significantly affects the function of antibody drugs, and has high complexity and high difficulty.

In some embodiments, the Fc region of the anti-Fc antibody or anti-Fc antibody fragment may have glycosylation modification.

This embodiment also provides a method for preparing the above-mentioned specific antibody delivery platform. The method may comprise the following steps: (A) oxidizing the anti-Fc antibody with an oxidizing agent to obtain an anti-Fc antibody containing an aldehyde group; and (B) reacting the anti-Fc antibody containing the aldehyde group obtained in step (A) with the above-mentioned protein-type nanoparticle to obtain a product, and then reducing the obtained product with a reducing agent.

In some embodiments, the anti-Fc antibody may be an anti-IgG-Fc antibody.

In some embodiments, the oxidizing agent may be sodium periodate. Further, the oxidation reaction time may be within a range of 1 h-4 h. Further, the oxidation reaction time may be within a range of 2 h-3 h. Further, the oxidation reaction in step (A) may be performed at a temperature in a range of 0° C.-8° C. in a dark environment. Further, after the oxidation reaction is completed, sodium periodate may be removed by ultrafiltration.

In some embodiments, the concentration of sodium periodate in the reaction system may be lower than 10 mM, which can prevent the oxidation of the hydroxyl groups on the sugar chains except the Fc segment to aldehyde groups.

In some embodiments, the concentration of the anti-Fc antibody in the reaction system in step (A) may be within a range of 0.8 mg/mL-1.2 mg/m L.

In some embodiments, the reducing reaction in step (B) may be performed at a temperature in a range of 0° C.-8° C.

In some embodiments, the Fc region of the anti-Fc antibody or anti-Fc antibody fragment may have glycosylation modification. The orthohydroxyl group on the sugar group of the Fc region is oxidized to an aldehyde group by an oxidant, then reacts with the amino group in the hydrophilic region of the protein to produce a Schiff base reaction, and then reduces the imino group to methylamino group to obtain the specific antibody delivery platform.

In some embodiments, the concentration of the protein-type nanoparticle in the reaction system in step (B) may be within a range of 0.4 mg/mL-0.6 mg/mL.

In some embodiments, the concentration of the anti-Fc antibody containing the aldehyde group in step (B) in the reaction system may be within a range of 0.02 mg/mL-0.03 mg/mL.

In some embodiments, the pH of the reaction between the anti-Fc antibody containing aldehyde group and the above-mentioned protein-type nanoparticle may be below 6.7, and the reaction time may be within a range of 0.5 h-1.5 h.

In some embodiments, the reducing agent in step (B) may be sodium borohydride, sodium cyanoborohydride, or sodium acetate borohydride. Further, the pH of the reducing reaction may be above 8.3, the reaction temperature may be within a range of 0° C.-8° C., and the reaction time may be within a range of 6 h-10 h. Further, the concentration of the reducing agent may be kept at a range of 0.4 mg/mL-0.6 mg/mL during the reducing reaction. In some embodiments, the reducing agent in step (B) may be sodium borohydride, and the concentration of sodium borohydride may be kept at a range of 0.4 mg/mL-0.6 mg/mL during the reducing process.

This embodiment also provides an application of the above-mentioned multi-specific antibody delivery platform in the delivery of multi-specific antibodies or in the preparation of a multi-specific antibody delivery system.

This embodiment also provides a multi-specific antibody delivery system. The multi-specific antibody delivery system may include the above-mentioned multi-specific antibody delivery platform and specific antibody.

In some embodiments, the multi-specific antibody delivery system may include at least one specific antibody, and the delivered antibody may be several different specific antibodies, which may have a strong affinity for the targets on the two types of cells to achieve an amplified anti-tumor effect. The multi-specific antibody delivery system may include at least two kinds of specific antibodies.

In some embodiments, the specific antibody may be anti-immune cell antibody and anti-tumor cell antibody. The anti-immune cell antibody may be anti-macrophage antibody, anti-natural killer (NK) cell antibody, and anti-T cell antibody. The multi-specific antibody delivery system of the present disclosure achieves the effect of enhancing tumor suppression by the interaction between the mediating immune cells and tumor cells.

This embodiment also provides an application of the above-mentioned protein-type nanoparticle or multi-specific antibody delivery platform or multi-specific antibody delivery system in the preparation of immunotherapeutic drug.

In some embodiments, the immunotherapy drug may be a tumor immunotherapy drug or an autoimmune disease treatment drug.

The multivalent multi-specific antibody delivery platform of the present disclosure may conveniently and quickly realize the binding of two or more antibodies. This specific antibody carrier has many potential advantages, such as bridging cells, bridging receptors, targeting heterogeneous tumors, targeting multiple immune checkpoints, targeting immune checkpoints and antigens, increasing antibody antigen affinity, prolonging circulation time of antibody, etc.

The present disclosure will be described in further detail below in conjunction with specific examples.

EXAMPLES

Sources and processing methods of raw materials used in the examples: human serum albumin (HSA), which is purchased from Equitech-Bio. Mouse serum albumin (MSA), which is purchased from Cusabio. Bovine serum albumin (BSA), which is purchased from Hefei Zhihong Tech Biotechnology Co., Ltd. The aliphatic polyester, which is purchased from Jinan Daigang Biotechnology Co., Ltd.

| Article number | Specific component | Viscosity | Molecular weight (K) |
|---|---|---|---|
| DG-75DLG055 | PLGA-COOR | 0.55 | 42 |
| DG-C050 | PCL-COOR | 0.5 | 45 |
| DG-95DLG045 | PLGA-COOR(LA/GA = 95/5) | 0.45 | 53 |
| DG-85DLG104 | PLGA-COOR(LA/GA = 85/15) | 1.04 | 168 |
| DG-75DLG018 | PLGA-COOR(LA/GA = 75/25) | 0.18 | 15 |
| DG-50DLG035 | PLGA-COOR(LA/GA = 50/50) | 0.35 | 30 |
| DG-DLH050 | PDLLA-COOH | 2.5 | 480 |
| DG-DLOH200 | PDLLA-OH | 2.0 | 460 |
| DG-D400 | PDLA-COOR | 4.0 | 700 |

-continued

| Article number | Specific component | Viscosity | Molecular weight (K) |
|---|---|---|---|
| DG-DL250 | PDLLA-COOR | 2.5 | 445 |
| DG-L030 | PLLA-COOR | 0.3 | 7.2 |
| DG-L070 | PLLA-COOR | 0.7 | 36 |
| DG-L150 | PLLA-COOR | 1.5 | 137 |
| DG-L200 | PLLA-COOR | 2.0 | 240 |
| DG-L400 | PLLA-COOR | 4.0 | 600 |
| DG-L600 | PLLA-COOR | 6.0 | 1100 |

The polyethylene glycol-modified aliphatic polyester, which is purchased from Xi'an Ruixi Biotechnology Company.

| Article number | Specific component | Molecular weight (K) |
|---|---|---|
| R-PL1053 | PEG5K-PLA16K | 5 K-16 K |
| R-PL1103 | PEG5K-PCL11.8K | 5 K-11.8 K |
| R-PL1001 | PEG5K-PLGA16K | 5 K-16 K |

Organic solvents such as chloroform (chloroform), dichloromethane, and ethyl acetate, which are purchased from Sinopharm Chemical Reagent Co., Ltd. Fluorescein isothiocyanate (FITC), which is purchased from Shanghai Aladdin Biochemical Technology Co., Ltd. Rhodamine B (RhoB), which is purchased from Shanghai Aladdin Biochemical Technology Co., Ltd. Goat anti-rat IgG-Fc antibody, which is purchased from Rockland Company. Sodium periodate, which is purchased from Shanghai Aladdin Biochemical Technology Co., Ltd. Sodium borohydride, sodium cyanoborohydride, and sodium acetate borohydride, which are purchased from Sigma-Aldrich company. Transmission electron microscope copper mesh, which is purchased from Haide Venture (Beijing) Biotechnology Co., Ltd.

The instrument type and company used in the examples: Ultrasonic cell disruptor, model of VCX130, Sonics Corporation of the United States. Desktop micro-refrigerated centrifuge, the model of Microfuge 20R, American Beckman company. Nanoparticle size and Zeta potential meter, model of Nano ZSE, Malvern of the United Kingdom. Rotary evaporator, model of RV10 digital V digital display type, Germany IKA company. Transmission electron microscope, model of Talos L120C, American Thermo Fisher Scientific Corporation. Scanning electron microscope, model of Merlin, German Zeiss company. Ultra-high performance nanoscale liquid chromatography (UPLC), model of ACQUITY UPLC H-Class, American Waters Company, which is equipped with a quaternary solvent manager (QSM) and a flow-through needle sampler design sample manager (SM-FTN). High performance liquid chromatograph (HPLC), model of Alliance 2695, Waters Company of the United State.

Example 1. Preparation of Albumin Aliphatic Polyester Nanoparticle

A chloroform solution of ester terminated L-polylactic acid (PLLA-COOR-1100K) is prepared at a concentration of 5 mg/mL, 10 mg of human serum albumin is dissolved in 1 mL of 0.9% sodium chloride aqueous solution, 1% (w/v) human serum albumin solution is prepared, 200 µL of ester-terminated L-polylactic acid chloroform solution is taken into a 15 mL centrifuge tube, 1 mL of 1% (w/v) human serum albumin solution is added into the 15 mL centrifuge tube, and emulsification is performed use ultrasonic cell disruptor. The ultrasonic power is 130 W, the amplitude is 50%, and the ultrasonic wave is performed for 5 s and stopped for 2 s, and a total ultrasonic time is 2 min. After performing the ultrasonic wave, the lotion is washed out of the centrifuge tube with ultrapure water, transferred to a 250 mL round bottom flask. The chloroform in the lotion of the round bottom flask is removed using a rotary evaporator in the order of vacuum degree of 300/120/70/40 mbar for 5 min in sequence. After the rotary evaporation, albumin aliphatic polyester nanoparticle is collected for standby, and named as particle 1.

For other preparation methods of nanoparticle based on different types of polyesters (different types, different optical activities, different terminal groups, different molecular weights) and different species of proteins, please refer to the preparation method of particle 1.

Example 2. Purification Method of Albumin Aliphatic Polyester Nanoparticle

Method 1 (centrifugation method): the particle 1 is centrifugated to remove the unassembled water-insoluble polyester at low speed (3000 rpm, 4° C.) for 10 min using a desktop micro freezing centrifuge, the supernatant is transferred to a new EP tube and centrifuged at high speed (15000 rpm, 4° C.) for 60 min to separate free albumin and nanoparticle, the free albumin in the supernatant is removed, and the particles of lower layer are suspended in 1×PBS for standby.

Method 2 (dialysis method): the particle 1 is dialysed using the dialysis bag (Shanghai Green Bird) with molecular weight of 14000 Da, dialysate is 1×PBS, the free albumin in the dialysis bag is completely replaced after dialysis of 8 times the volume, and the albumin aliphatic polyester nanoparticle in the dialysis bag is taken for standby.

Example 3. Particle Size Characterization of Albumin Aliphatic Polyester Nanoparticle The concentration of the purified particle in Example 2 is diluted to 0.1 mg/mL (the concentration is based on the protein, unless otherwise specified, the concentration of the particle involved in this disclosure is defined based on the protein). The hydration diameter of nanoparticle is detected in the cuvette by using nanoparticle size and Zeta potential meter. The corresponding particle size distribution diagrams of nanoparticles are shown in FIGS. 1-8, and the average particle size distribution is summarized as follows.

| Name | Type of aliphatic polyester | Type of protein | Particle size |
|---|---|---|---|
| Particle 1 | PLLA-COOR-1100K | HSA | 167.5 ± 3.5 |
| Particle 2 | PLLA-COOR-1100K | BSA | 146.2 ± 2.3 |
| Particle 3 | PLLA-COOR-1100K | MSA | 177.6 ± 3.4 |
| Particle 4 | PCL-COOR-45K | HSA | 160.9 ± 3.4 |
| Particle 5 | PLGA-COOR-42K | HSA | 103.9 ± 2.4 |
| Particle 6 | PDLA-COOR-700K | HSA | 128.8 ± 0.8 |
| Particle 7 | PDLLA-COOR-445K | HSA | 103.0 ± 0.7 |
| Particle 8 | PLGA(LA/GA = 95/5)-53K | HSA | 74.8 ± 0.4 |
| Particle 9 | PLGA(LA/GA = 85/15)-168K | HSA | 76.0 ± 0.7 |
| Particle 10 | PLGA(LA/GA = 75/25)-15K | HSA | 109.5 ± 1.1 |
| Particle 11 | PLGA(LA/GA = 50/50)-30K | HSA | 116.8 ± 1.8 |
| Particle 12 | PDLLA-OH-460K | HSA | 140.8 ± 3.5 |
| Particle 13 | PDLLA-COOH-480K | HSA | 144.1 ± 1.4 |
| Particle 14 | PLLA-COOR-7.2K | HSA | 115.8 ± 1.7 |
| Particle 15 | PLLA-COOR-36K | HSA | 102.9 ± 0.7 |
| Particle 16 | PLLA-COOR-137K | HSA | 108.5 ± 1.5 |
| Particle 17 | PLLA-COOR-240K | HSA | 87.4 ± 1.4 |
| Particle 18 | PLLA-COOR-600K | HSA | 119.3 ± 1.1 |

-continued

| Name | Type of aliphatic polyester | Type of protein | Particle size |
|---|---|---|---|
| Particle 19 | PEG5K-PLGA16K | HSA | 137.2 ± 1.4 |
| Particle 20 | PEG5K-PCL11.8K | HSA | 134.1 ± 2.7 |
| Particle 21 | PEG5K-PLA16K | HSA | 131.6 ± 1.5 |

Figure 8:
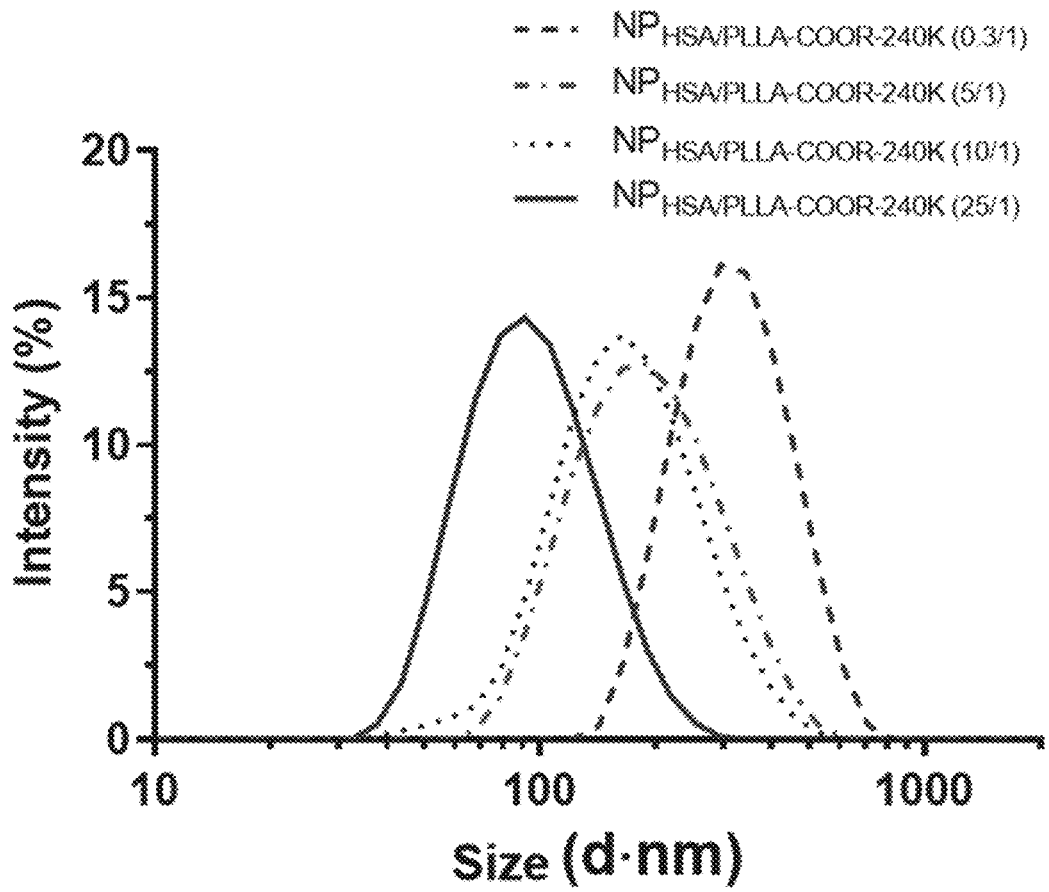
FIG. 8 is a diagram illustrating the particle size of particles of the human serum albumin and aliphatic polyester in different mass ratios according to some embodiments of the present disclosure.

Example 4. Preparation of Albumin Aliphatic Polyester Nanoparticle in Different Ratios A chloroform solution of ester-terminated L-polylactic acid (PLLA-COOR-240K) at a concentration of 5 mg/mL, 10 mg of human serum albumin is taken in 1 mL of 0.9% sodium chloride aqueous solution, and 1% (w/v) human serum albumin solution is prepared. The polyester and albumin are mixed according to a mass ratio of the polyester to albumin of 1:0.3, 1:5, 1:10, 1:25, and the albumin aliphatic polyester nanoparticle is prepared according to the preparation method in Example 1, purified according to the centrifugation method in Example 2, and named as particle 22 (1:0.3), particle 23 (1:5), particle 24 (1:10), and particle 25 (1:25). The paricles are characterized according to the method in Example 3, the results are shown in FIG. 8, the mass ratio of albumin to aliphatic polyester is too high, resulting in low particle size of nanoparticle, which is not conducive to mediating the multivalent function of specific antibody. However, the mass ratio of albumin to aliphatic polyester is too low, which may result in larger particle size due to insufficient assembly.

Figure 9:
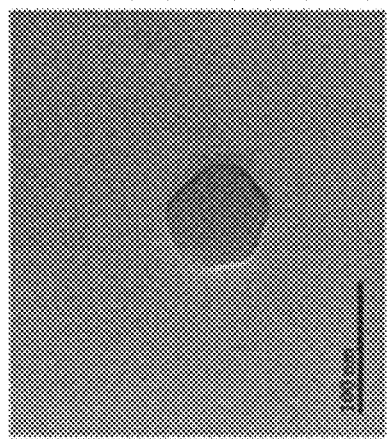
FIG. 9 is a transmission electron microscope image of particles of human serum albumin and aliphatic polyester in different mass ratios according to some embodiments of the present disclosure.
Figure 9:
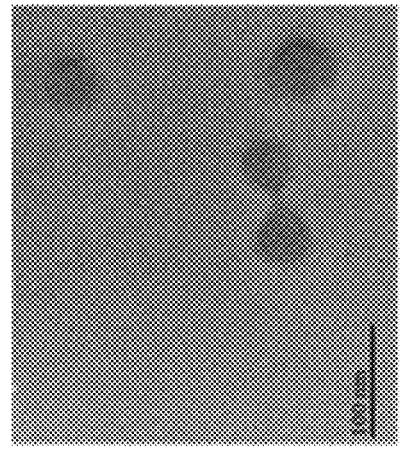
Figure 9:
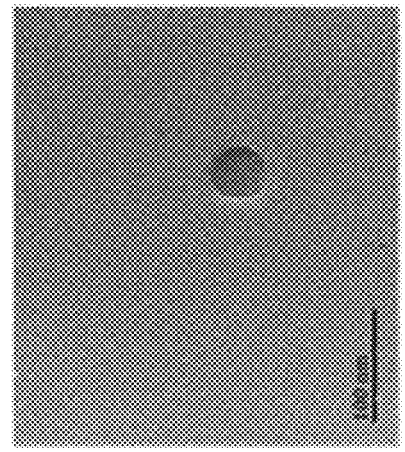
Figure 9:
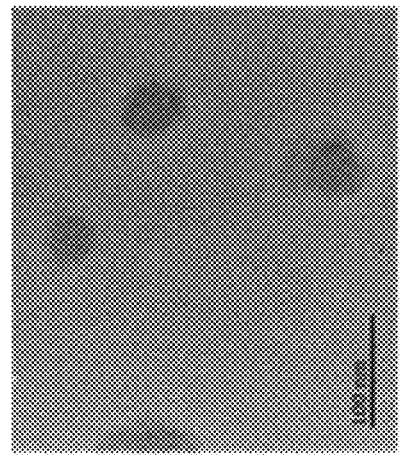

Example 5. Observation of the Shape of Albumin Aliphatic Polyester Nanoparticle after Centrifugal Purification by Transmission Electron Microscope According to the preparation method in Example 4, particle 22, particle 23, particle 24, and particle 25 are prepared. After the particles are purified according to the method in Example 2, the concentration of the nanoparticles is diluted to 0.1 mg/mL, 10 μL particles is added to the transmission electron microscope copper mesh, and the water is evaporated for 8 h and observed under the transmission electron microscope. As shown in FIG. 9, the particles with different ratios of aliphatic polyester and albumin are all independent spherical shapes.

Figure 10:
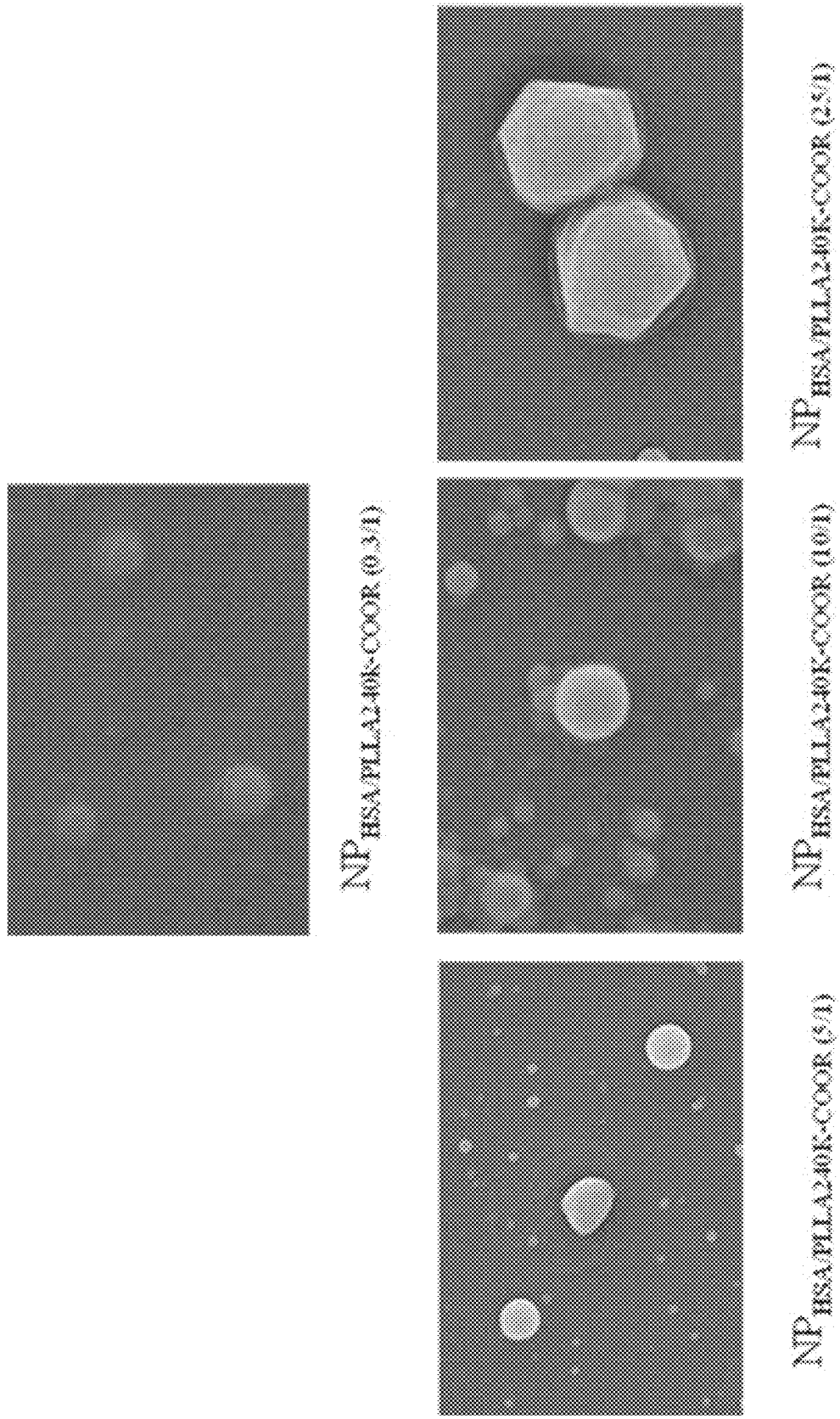
FIG. 10 is a scanning electron microscope image of particles of human serum albumin and aliphatic polyester in different mass ratios according to some embodiments of the present disclosure.

Example 6. Observation of Surface Morphology of Albumin Aliphatic Polyester Nanoparticle after Centrifugal Purification by Scanning Electron Microscope According to the preparation method in Example 4, particles with different ratios of aliphatic polyester and albumin (1:0.3, 1:5, 1:10, 1:25) are prepared. After the particles are purified according to the method in Example 2, the concentration of the nanoparticles is diluted to 0.1 mg/mL, 10 μL solution is added on tin foil, and observed under a scanning electron microscope after the water is evaporated for 8 h. As shown in FIG. 10, the higher the ratio of albumin is, the looser the surface structure of the particles is, and the lower the ratio of albumin is, the more unstable the particles is, and the particles observed under the scanning electron microscope are trapped in the protein released by disintegration, which further indicates the preferred ratio of polyester and albumin is 1:10.

Example 7. Detection of the Ratio of Albumin and Aliphatic Polyester in Albumin Aliphatic Polyester Nanoparticle Human serum albumin is labeled with fluorescein isothiocyanate (FITC) in advance, polycaprolactone (PCL-COOR) is labeled with rhodamine B (RhoB), and free fluorescent reagents are removed by dialysis or ultrafiltration to obtain fluorescent labeled albumin (FITC-HSA) and rhodamine B labeled polycaprolactone (RhoB-PCL-COOR). Four fluorescently labeled particles NPFITC-HSA/RhoB-PCL-COOR are prepared with reference to the ratio of aliphatic polyester and albumin described in Example 5. Purified fluorescent nanoparticles are obtained by referring to the centrifugal purification method in Example 2, and named as particle 22' (1:0.3), particle 23' (1:5), particle 24' (1:10), and particle 25' (1:25).

(1) Detecting the content of albumin in nanoparticles using HPLC method: after diluting the purified particles by a certain number of times, the fluorescence intensity atexcitation wavelengths of488 nm and 540 nm and the UV absorption value at a wavelength of 280 nm are detected by high performance liquid chromatography (Waters, Alliance 2695), and the FITC-HSA is used as the standard sample by gradient dilution to obtain the concentration of free albumin in the particles. The content of albumin in the particles may be calculated according to the recovery rate and centrifugation efficiency of the particles.

Liquid phase conditions: Chromatographic column type: Ultrahydrogel Column, 500 Å, 10 μm, 7.8 mm×300 mm. Mobile phase: 1×PBS. Mobile phase flow rate: 0.6 mL/min. Detector: a combination of UV (280 nm)-fluorescence (488 nm, 540 nm). Injection volume: 10 μL.

(2) Detecting the content of aliphatic polyester in nanoparticles using extraction method: some of the purified nanoparticles are extracted with acetonitrile or chloroform, the fluorescence intensity of rhodamine B (excitation light of 540 nm and emission light of 590 nm) is detected with a full wavelength scanning multi-function reader (Thermo Scientific Varioskan Flash), and RhoB PCL-COOR is used as the standard sample by gradient dilution to obtain the concentration of aliphatic polyester in the nanoparticles. The content of aliphatic polyester participating in the assembly of nanoparticles may be calculated according to the recovery rate and centrifugal efficiency of nanoparticles.

Detection method for the recovery rate of albumin aliphatic polyester nanoparticles: particles are prepared according to the method in Example 1, the unassembled water-insoluble polyester is removed using low-speed centrifugation, and the supernatant is freeze-dried to obtain the powder, a mass of the powder is recorded as $m_1$, and the total mass of albumin and polyester is recorded as $m_0$, then the recovery rate of particles is $m_1/m_0 \times 100\%$.

Detection method of centrifugation efficiency of albumin aliphatic polyester nanoparticles: polyester is labeled with rhodamine B (RhoB) in advance, nanoparticles containing fluorescent polyester are obtained with reference to the particle preparation method in Example 1, the unassembled water-insoluble polyester are removed using low-speed centrifugation with referrence to the nanoparticle purification method (centrifugation) in Example 2, the supernatant is further centrifuged at high speed to obtain the supernatant and precipitate, and a small amount of supernatant is added with five times the volume of DMSO for destruction. The precipitate is re suspended with 100 μL ultrapure water, and a small amount of particle suspension is added with 200 times volume of DMSO for destruction at room temperature for 2 h. Then, the fluorescence intensity of Rhodamine B (excitation light of 540 nm and emission light of 590 nm) in the supernatant and precipitate are detected using a Thermo Scientific Varioskan Flash, and the RhoB-PCL-COOR is used as the standard sample with DMSO through gradient dilution. It may be obtained that the relative content of polyester in the supernatant and precipitation is $m_1$, $m_2$, so the centrifugal efficiency of particles is $m_2/(m_1+m_2) \times 100\%$.

Figure 11:
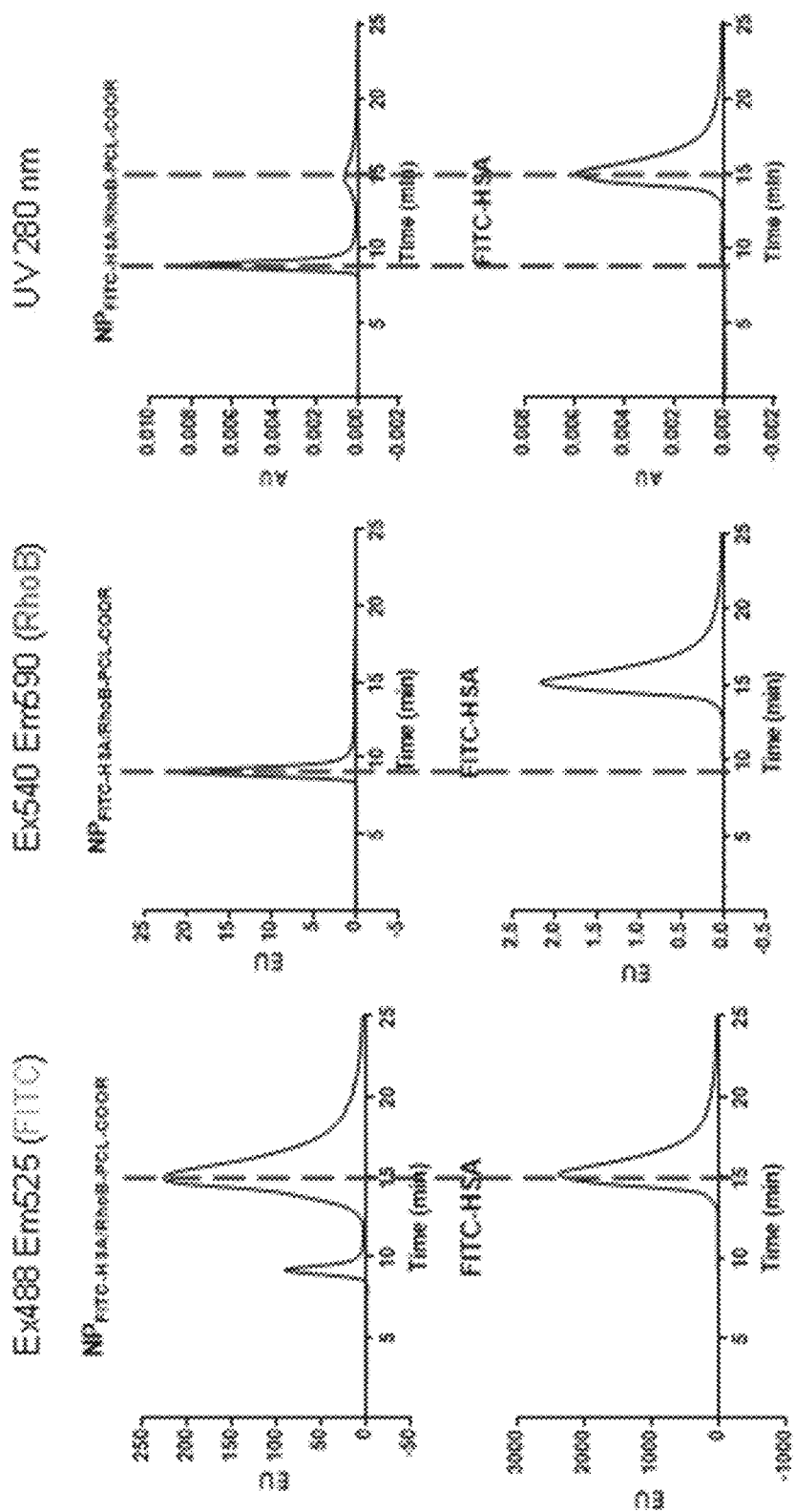
FIG. 11 is a diagram illustrating the actual ratio of human serum albumin and aliphatic polyester in the particles characterized by high performance liquid chromatography according to some embodiments of the present disclosure.

The centrifugation efficiency and recovery rate of particle 22', particle 23', particle 24', and particle 25', and relative ratio of albumin/aliphatic polyester polymer are shown in the table below. The particle 24 ' and FITC-HSA characterized by liquid chromatography are shown in FIG. 11. As can be seen from the data in the following table, the preferred ratio of aliphatic polyester to albumin in the preparation of albumin polyester nanoparticle in the present dislcosure is 1:10, its comprehensive utilization rate (recovery rate× centrifugal efficiency) is higher, and more albumin may be assembled with less hydrophobic polyester.

| Mass ratio | Recovery rate (%) | Centrifugal efficiency (%) | Recovery rate*Centrifugal efficiency | Ratio of free protein to the purified particle | Albumin:Polyester |
|---|---|---|---|---|---|
| 1:0.3 | 40.0 | 86.1 | — | | |
| 1:5 | 55.7 | 83.5 | 0.47 | 4.89% | 18.9:1 |
| 1:10 | 86.4 | 74.6 | 0.64 | 5.81% | 33.5:1 |
| 1:25 | 90.1 | 30.5 | 0.27 | 4.43% | 132.3:1 |

Figure 12:
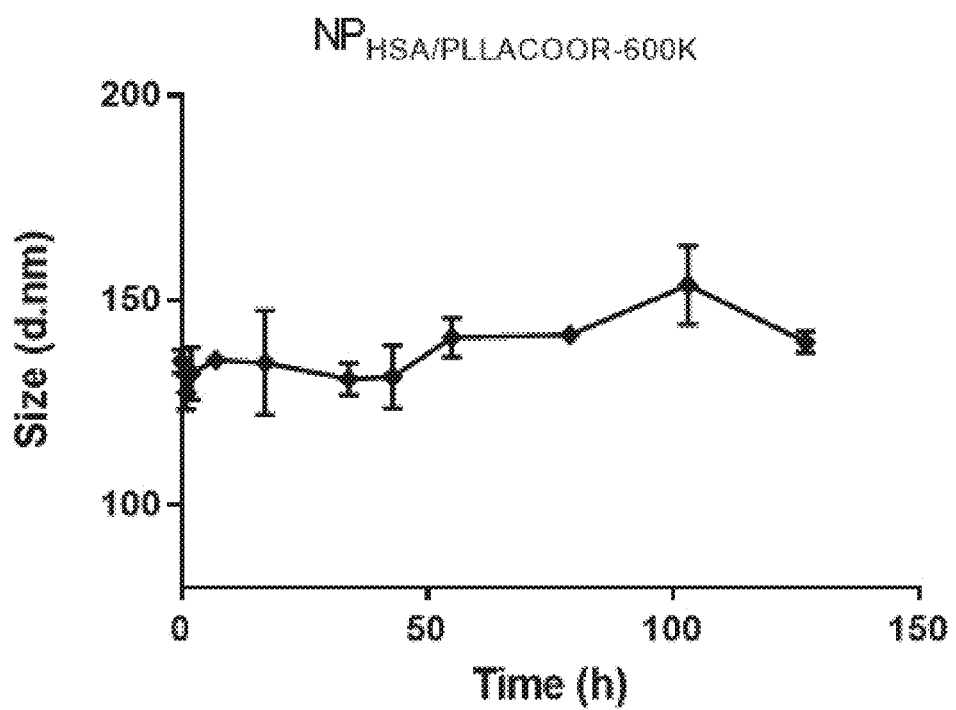
FIG. 12 is a diagram illustrating the serum stability of the composition obtained by centrifugation-resuspension of particles of albumin and aliphatic polyester according to some embodiments of the present disclosure.

Example 8. Serum Stability of the Composition Obtained by Centrifugation-Resuspension of Albumin Aliphatic Polyester Nanoparticle Particle 18 is prepared according to the preparation method in Example 1, and the nanoparticle is purified by the centrifugation method in Example 2. The purified nanoparticle is diluted to 1 mg/mL, diluted to 1×PBS using 10×PBS, and added with 10% FBS. The particle size and size distribution of nanoparticles are measured by nanoparticle size and Zeta potential meter at 0 h, 1 h, 2 h, 4 h, 6 h, 8 h, 12 h, 24 h, 36 h, 48 h, 60 h, 72 h, 84 h, 96 h, 108 h, 120 h, 144 h, respectively. As shown in FIG. 12, during the observation period of up to one week, the particle size of the nanoparticles has no significant change, and the particle size distribution has no huge fluctuation, which indicates that the nanoparticles of the disclosure may maintain the stability of the hydration radiusfor as long as one week.

Example 9. Albumin Release Behavior of the Composition Obtained by Centrifugation-Resuspension of Albumin Aliphatic Polyester Nanoparticle Particles 1 and 14-18 are prepared according to the preparation method in Example 1, and the particles are purified by the centrifugation method in Example 2. In the albumin release experiment of nanoparticles, the purified particles are firstly diluted to 1 mg/mL, and then 100 μL of the particles are taken at different time points and centrifuged at 15000 rpm for 1 h at 4° C. to separate the particles and supernatant (containing free HSA), and the albumin behavior of the nanoparticles is observed by measuring the ratio of albumin released from the particles in the supernatant. The concentration of free protein in the supernatant is detected by the following two methods.

Figure 13:
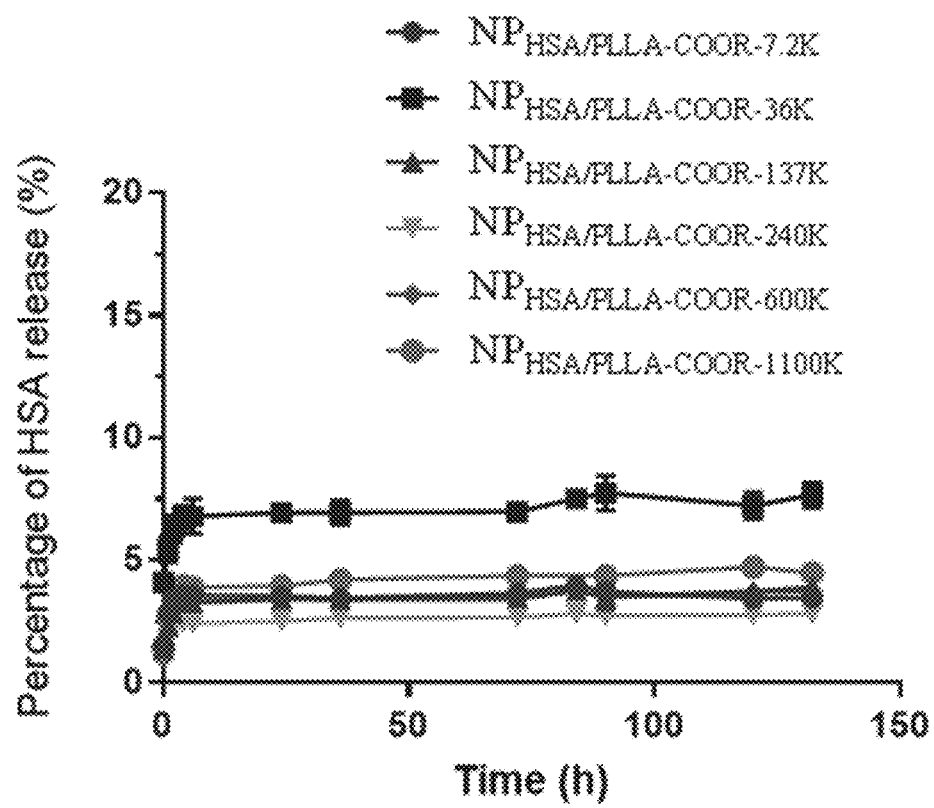
FIG. 13 is a diagram illustrating the protein release behavior of the composition obtained by centrifugation-resuspension of particles of albumin and aliphatic polyester (different molecular weight) according to some embodiments of the present disclosure.

(1) BCA protein concentration detection (BCA assay): The standard samples are prepared with HSA for preparing nanoparticles, and the ratio of free albumin from nanoparticles in the supernatant is detected using BCA assay. As shown in FIG. 13, the albumin release ratios of all particles are lower than 6%.

Figure 14:
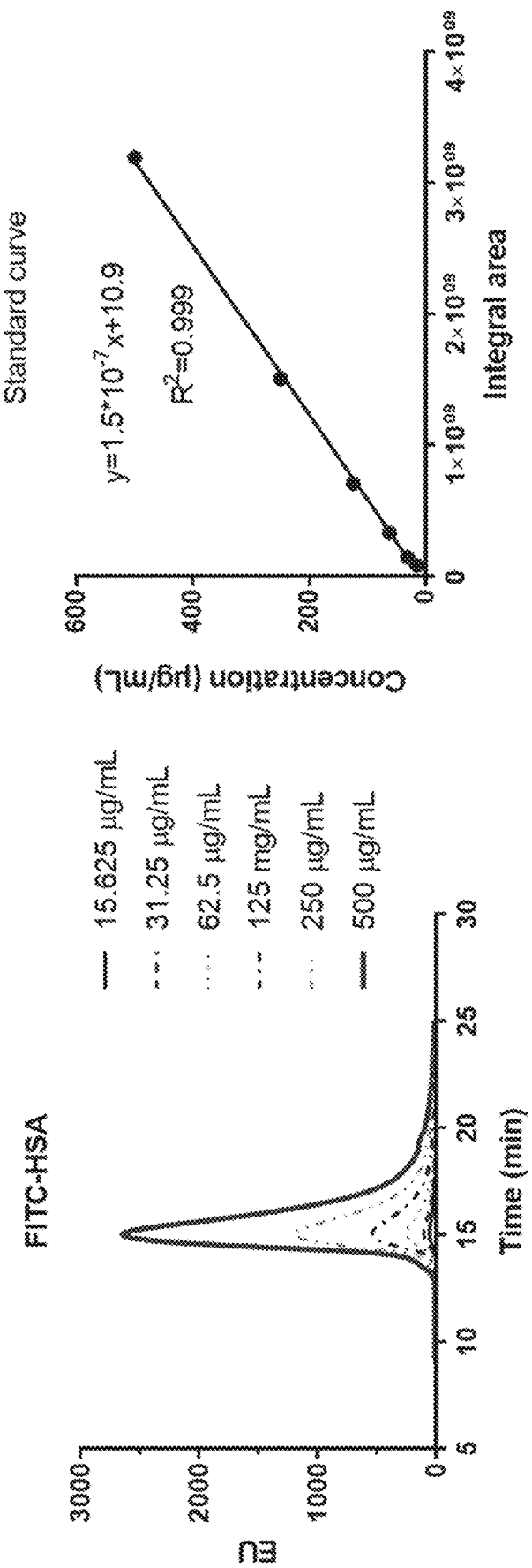
FIG. 14 is a FITC-HSA standard curve established by the high performance liquid chromatography according to some embodiments of the present disclosure.

(2) High performance liquid chromatography assay (HPLC method): the ratio of albumin released during the standing process after purification of particles is detected using HPLC method. With reference to the method of Example 6, taking particle 24 as an example, after diluting the purified particle to a certain multiple, the fluorescence intensity at an excitation wavelength of 488 nm and the UV absorption value at a wavelength of 280 nm are dedtected using high-performance liquid chromatography, and FITC-HSA is used as the standard sample by gradient dilution. The FITC-HSA standard sample is characterized by high performance liquid chromatography and the obtained standard curve is shown in FIG. 14. The concentration of free albumin in the particles and the ratio of free albumin from particles in the supernatant may be calculated using this standard curve. The results also show that no more than 6.5% of albumin is released from the particles.

The above results indicate that particles 1 and 14-18 only release less than 6.5% of albumin for a week, the nanoparticles have good stability, and the albumin bound by hydrophobic interaction may be stably assembled.

Example 10. Albumin Aliphatic Polyester Nanoparticle Bonded with Anti-IgG-Fc Antibody (αFc-NP)

1) Goat anti-rat IgG-Fc antibody is diluted with ultrapure water to 1.0 mg/mL, added by sodium periodate aqueous solution to reach a final concentration of 7.5 mM, and oxidized at 4° C. in the dark for 2 h. After the oxidation reaction, the aldehyde group of the antibody is quickly detected using the Purpald method. Under the condition of 0.05 M sodium acetate buffer (pH=4.2), sodium periodate is removed using 100 kDa ultrafiltration tube to ultrafilter 2-3 times. After recovering the oxidized antibody, the antibody concentration is quickly detected using Nanodrop A280.

Figure 19:
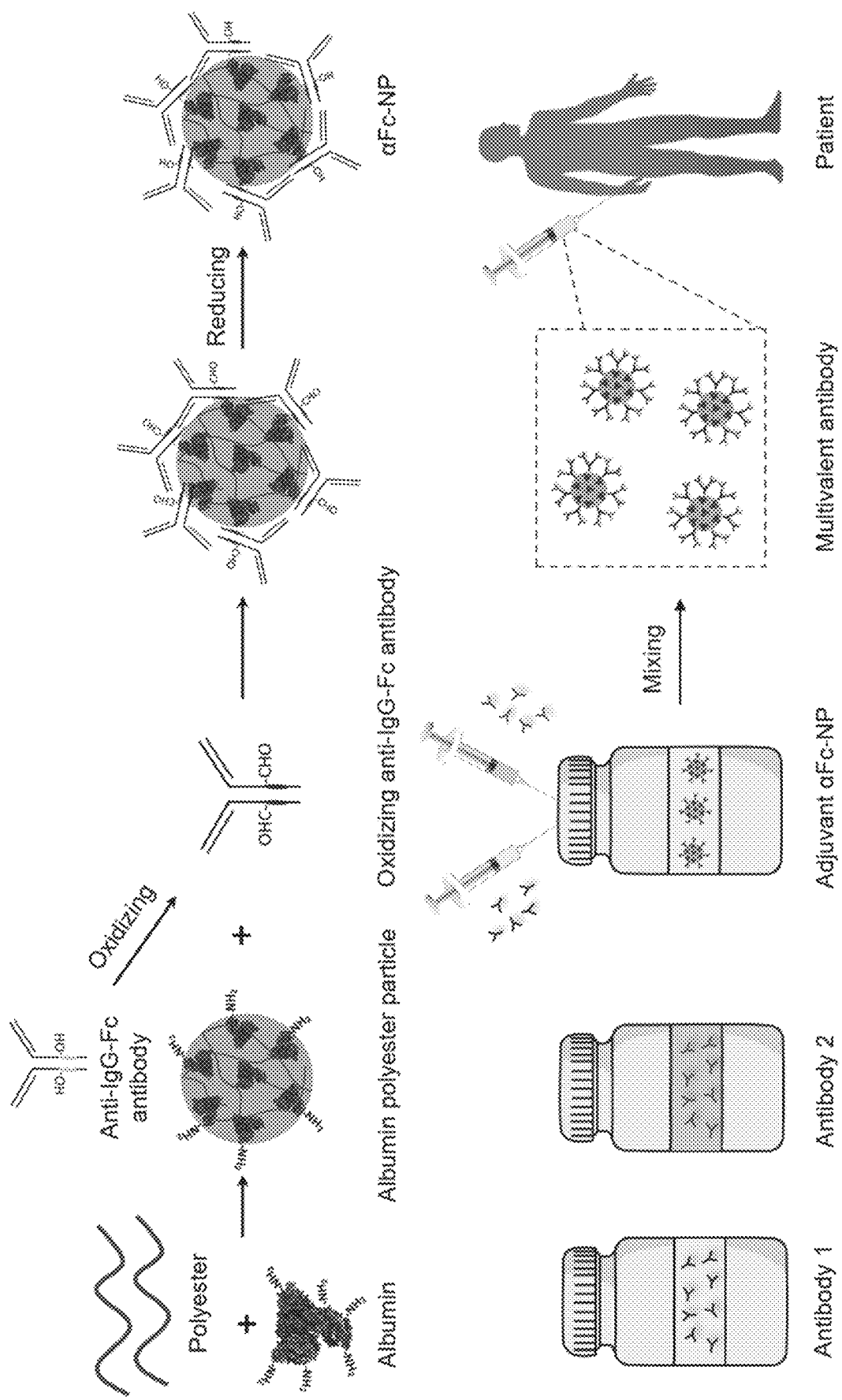
FIG. 19 is a schematic diagram of the preparation and application of αFc-NP according to some embodiments of the present disclosure.

2) Particle 1 is diluted with ultrapure water to 0.5 mg/mL, and the above-mentioned oxidized antibody is added at 0.025 mg/mL, 1 M acetate buffer is used to adjust the pH of the reaction system to below 6.7, and mixed thoroughly for 1 h. After the mixed adsorption, 0.1 M NaOH is used to adjust the pH of the reaction system to above 8.3, and then reaction is performed at 4° C. for 8 h. During the reaction, 10 mg/mL sodium borohydride is added in 4 times to make the concentration as 0.5 mg/m L. After the reaction, centrifugation is performed at 15,000 rpm at 4° C. for 1.0 h, the supernatant is retained for later characterization, the particles of lower layer are suspended with equal volume of ultrapure water and centrifuged twice again to obtain albumin polyester particles bonded with goat anti rat IgG-Fc antibody (αFc-NP) (as shown in FIG. 19). The particle size is characterized as 185.3 nm, and the polydispersity index is 0.153.

Example 11. Efficiency of Albumin Aliphatic Polyester Nanoparticle Binding Anti-IgG-Fc Antibody Characterized Using Polyacrylamide Gel Electrophoresis (SDS-PAGE)

Figure 15:
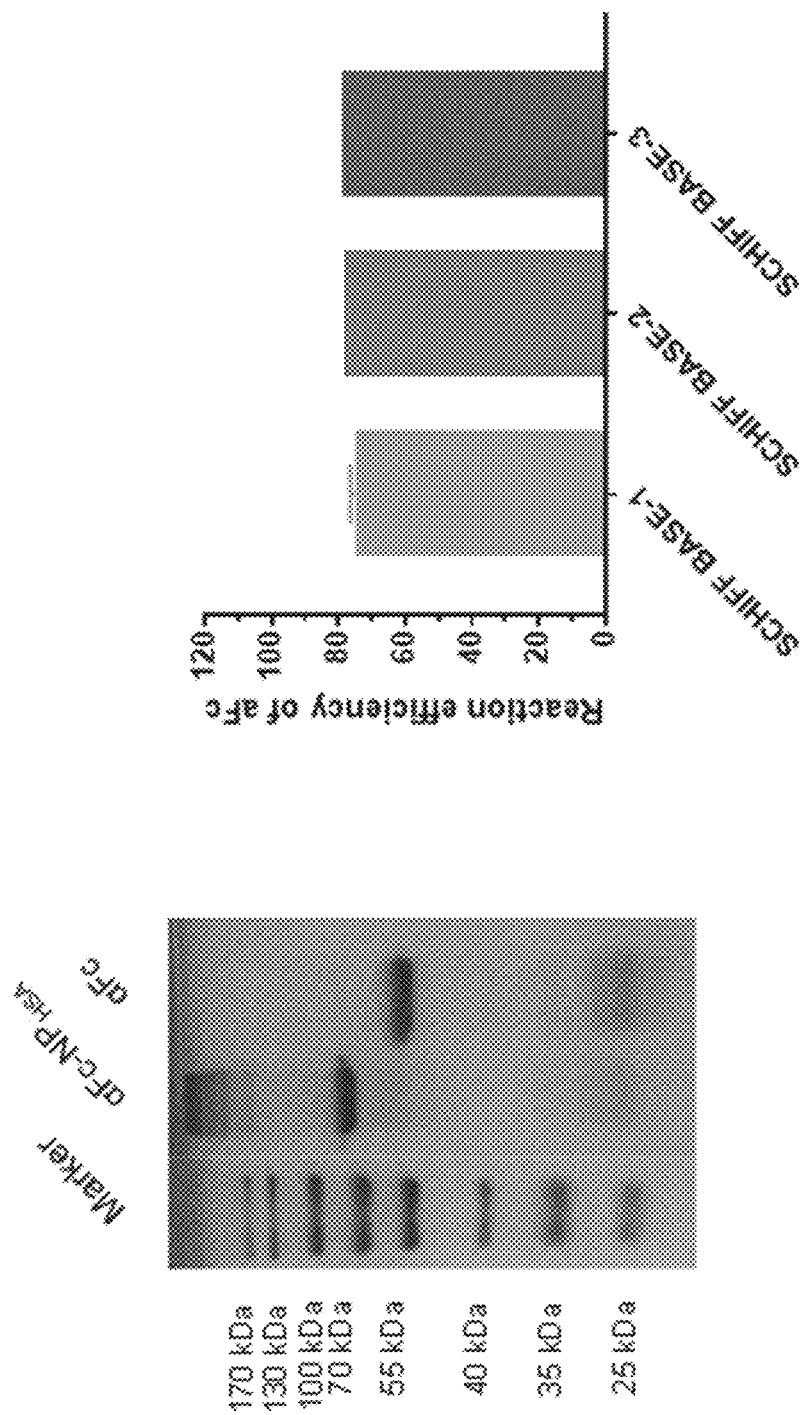
FIG. 15 is a diagram illustrating particles of albumin and aliphatic polyester binding αFc antibody according to some embodiments of the present disclosure.

The particles in the lower layer after the reaction in Example 10 is taken, 25 μL of 1×PBS is added to the particles for standing and resuspending, reducing protein and loading buffer are added ton the particles, and αFc bonding effect is qualitatively observed by characterizing the ratio of heavy chain and light chain of released antibody by polyacrylamide gel electrophoresis (SDS-PAGE). As shown in FIG. 15, the anti-IgG-Fc antibody of αFc-NP is significantly reduced compared with the heavy chain of the free antibody, indicating that its binding mode is in line with expectations.

Example 12. The Efficiency of Albumin Aliphatic Polyester Nanoparticle Binding Anti IgG-Fc Antibody Characterized Using Enzyme Linked Immunosorbent Assay (ELISA)

The supernatant after the reaction in Example 10 is taken, and the amount of goat anti-rat IgG-Fc antibody bound to the particles is tested by enzyme-linked immunosorbent assay (ELISA), which is caculated by subtracting the residual free antibody in the supernatant after centrifugation from the total amount of feed. The reaction efficiency of the anti-IgG-Fc antibody is shown in FIG. 15. The results show that the reaction efficiency of the anti-IgG-Fc antibody and the albumin polyester nanoparticles by forming a Schiff base is higher than 80%.

Example 13. Affinity Characterization of αFc-NP Binding Functional Antibody

In order to more conveniently characterize whether the affinity of αFc-NP binding to functional antibodies changes, the anti-IgG-Fc antibody bound to the particle is replaced with an anti-PD-1 antibody, namely αPD-1-NP, and the preparation method of the particle is referred to the preparation method in example 1. For the binding of anti-PD-1 antibody, refer to Example 10. The characterization method adopts the ELISA method, and the specific steps are as follows:
(1) coating Recombinant PD-1 antigen (Sino Biological Inc.) on a polystyrene plate (Corning) in advance, incubating at 37° C. for 2 h, washing the plate twice with 1×PBST, and patting dry;
(2) adding 1×PBS containing 2% BSA, sealing at room temperature for 1 h, washing the plate twice with 1×PBST after sealing, and patting dry;
(3) adding samples and incubating at room temperature for 1 h, the samples being gradient diluted anti-PD-1 antibody (BioXcell) and αPD-1-NP, washing the plate 6 times with 1×PBST and patting dry;
(4) adding HRP antibody (Sino Biological Inc.), incubating at room temperature for 30 min, washing the plate 6 times with 1×PBST, and patting dry;
(5) adding TMB substrate (Abcam) and incubating for 10 min under dark conditions; and
(6) adding 2 M H2SO4 to stop the color development, and detecting the absorbance of the sample at wavelength of 450 nm and 630 nm using a microplate reader.

The dissociation constant Kd value is calculated using the software "Graphpad Prism 7.00" and Kd is converted to the binding constant Ka value for comparing the affinity changes between αPD-1-NP and PD-1.

Figure 16:
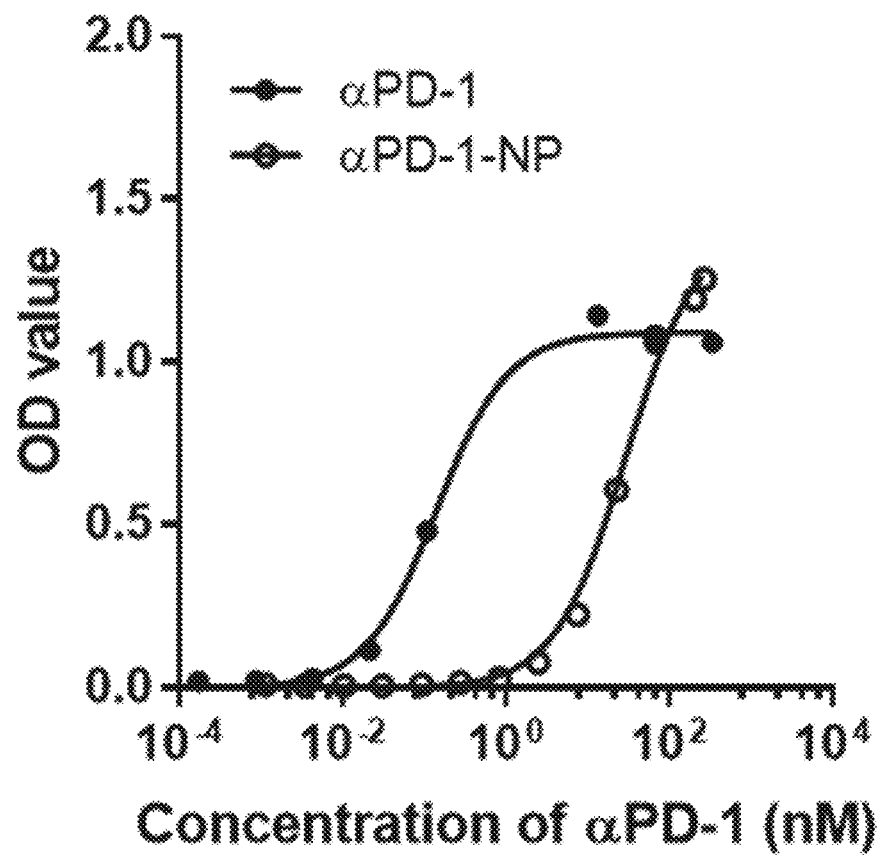
FIG. 16 is a diagram for determination of affinity of particles of albumin and aliphatic polyester binding antibody according to some embodiments of the present disclosure.

The results are shown in FIG. 16, the dissociation constant of αPD-1 to PD-1 is 1.41E-07, and the affinity of αPD-1-NP to PD-1 is 2.88E-5, the results show that albumin aliphatic polyester particle after binding to the antibody still maintains a high affinity for the functional antibody.

Example 14. Method of αFc-NP Binding a Functional Antibody (αFc-NP (αPD-1/αPD-L1))

The albumin polyester particle (αFc-NP) bound with goat anti-rat IgG-Fc antibody obtained in Example 10 and the total amount of functional antibody (αPD-1/αPD-L1=1/1) is bound according to a ratio of 1:1 at 4° C. for 6 h to obtain αFc-NP (αPD-1/αPD-L1), a particle size of αFc-NP (αPD-1/αPD-L1) is 203.2 nm, and a polydispersity index of αFc-NP (αPD-1/αPD-L1) is 0.182.

Figure 17:
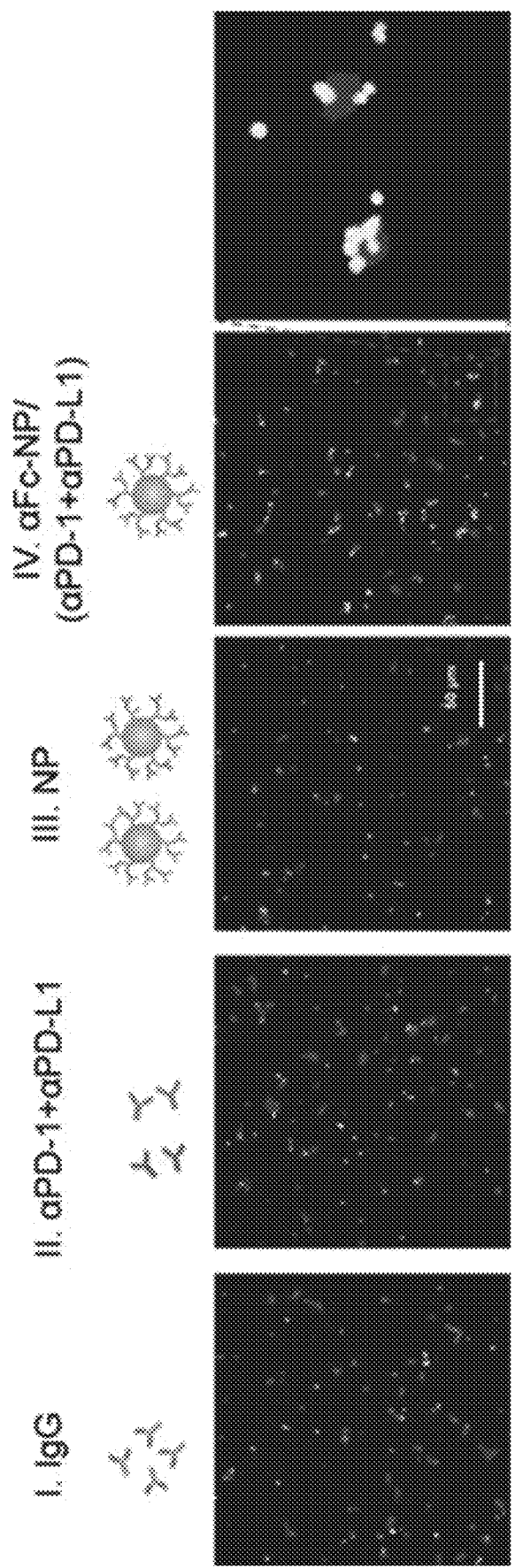
FIG. 17 is an observation image of αFc-NP (αPD-1/αPD-L1) promoting the interaction between tumor cells and T cells through a laser confocal observation according to some embodiments of the present disclosure.

Example 15. Observation Diagram of αFc-NP (αPD-1/αPD-L1) Promoting the Interaction Between Tumor Cells and T Cells Using Laser Confocal Observation A mouse melanoma cell line (B16-F10) is selected to explore the interaction of αFc-NP with therapeutic antibody and cells. After T cells are labeled with CFSE, T cells are co-cultured with B16-F10 cells (expressing mCherry fluorescent protein), and three experimental groups are set respectively, such as mix free (αPD-1&αPD-L1), separate NPs (αFc-NPαPD-1 & αFc-NPαPD-L1), αFc-NPαPD-1&αPD-L1 ([IgG]=20 μg/mL, [αPD-1]=10 μg/mL, [αPD-L1]=10 μg/mL). The corresponding particles (refer to example 10) or antibody components are added respectively, and after 4 h of incubation, the unbound particles and T cells that do not interact with tumor cells arewashed. As shown in FIG. 17, compared with other groups, in the group of αFc-NP/2Abs, more T cells are co located with tumor cells, indicating that the particles may promote the interaction between the two cells.

Example 16. Detection of αFc-NP (αPD-1/αPD-L1) Promoting T Cells to Kill Tumor Cells by H 33342 Release Method A mouse melanoma cell line (B16-F10) is selected to explore the effect of αFc-NP bound with therapeutic antibodies promoting T cells to kill tumor cells. Use T cells are specifically activated using CD3 antibody, and B16-F10-ova is stained with H 33342, T cells and B16-F10-ova (H 33342) are mixed in a ratio of 1:10. PBS, mix free (αPD-1&αPD-L1), separate NPs (αFc-NP$_{αPD-1}$ & αFc-NP$_{αPD-L1}$), and αFc-NP$_{αPD-1\&αPD-L1}$ ([IgG]=50 μg/m L, [αPD-1]=25 μg/mL, [αPD-L1]=25 μg/mL) are set, and the incubation is performed for 12 h and 24 h. After incubation, Triton X-100 is added to the maximum release group to destroy cells and release fluorescent dyes, only tumor cells are found in the naturally release group, then killing activity of T cells=(OD of experimental group−OD of natural release group)/(OD of maximum release group−OD of natural release group)× 100%.

Figure 18:
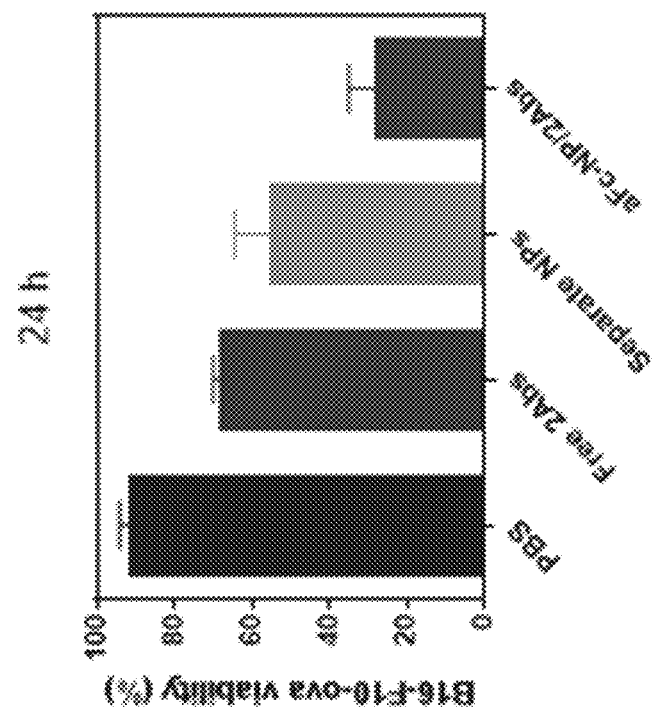
FIG. 18 is a diagram for detection of αFc-NP (αPD-1/αPD-L1) promoting T cells to kill tumor cells by H 33342 release method according to some embodiments of the present disclosure.
Figure 18:
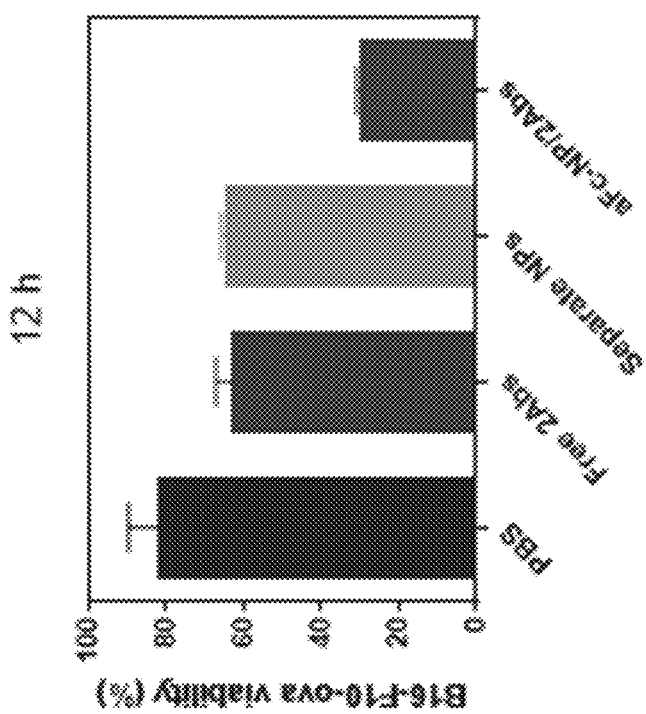

As shown in FIG. 18, αFc-NPαPD-1 & αPD-L1 show significant ability to promote T cells to kill tumor cells at different time points.

The technical features of the above-described embodiments can be combined arbitrarily. For the sake of brevity, all possible combinations of the technical features in the above embodiments are not described. However, the combinations of these technical features should be regarded as the scope described in the present disclosure as long as there is no contradiction between the combinations of these technical features.

The above embodiments merely illustrate some embodiments of the present disclosure, which are descibed specifically and in detailed, but should not be understood as a limit on the scope of the present disclosure. It should be noted that for those skilled in the art, without departing from the concept of the present disclosure, some modifications and improvements can also be made, which all belong to the protection scope of the present disclosure. Therefore, the protection scope of the present disclosure should be subject to the appended claims.

What is claimed is:

1. A multi-specific antibody delivery platform, which is formed by bonding a protein-type nanoparticle with an anti-Fc antibody through a chemical bond, wherein
the protein-type nanoparticle includes polyester and a protein with a hydrophobic domain, and the hydrophobic domain of the protein is bound with the polyester through hydrophobic interaction, wherein the protein is albumin or a cell wall protein, and the protein has a same species as a recipient of the delivered specific antibody, wherein
the anti-Fc antibody is an anti-IgG-Fc antibody;
a weight ratio of the polyester to the protein is within a range of 1:(9-11);
a Fab domain of the anti-Fc antibody is non-covalently bound with an Fc domain of a delivered specific antibody; and
the delivered specific antibody has a same species as an Fc segment recognized by the anti-Fc antibody.

2. The multi-specific antibody delivery platform of claim 1, wherein the protein is at least one of a human serum albumin, a bovine serum albumin, a mouse serum albumin, an ovalbumin, a protein A, or protein G.

3. The multi-specific antibody delivery platform of claim 1, wherein the polyester is aliphatic polyester or polyethylene glycol-modified aliphatic polyester.

4. The multi-specific antibody delivery platform of claim 3, wherein the aliphatic polyester is at least one of polylactic acid, polyglycolide, poly(glycolide-co-lactide), or polycaprolactone; and the polyethylene glycol-modified aliphatic polyester is at least one of polyethylene glycol-modified polylactic acid, polyethylene glycol-modified polyglycolide, polyethylene glycol-modified poly(glycolide-co-lactide), or polyethylene glycol-modified polycaprolactone.

5. The multi-specific antibody delivery platform of claim 4, wherein the aliphatic polyester is polylactic acid; the polylactic acid is L-polylactic acid, D-polylactic acid, or racemic polylactic acid; and a terminal group of the polylactic acid is at least one of an ester group, a carboxyl group, or a hydroxyl group.

6. The multi-specific antibody delivery platform of claim 5, wherein the polylactic acid is the L-polylactic acid, a terminal group of the L-polylactic acid is the ester group, and a molecular weight of the L-polylactic acid is within a range of 7200 Daltons-1100000 Daltons.

7. The multi-specific antibody delivery platform of claim 4, wherein a ratio of LA/GA in the poly(glycolide-co-lactide) is within a range of 95/5-50/50.

8. The multi-specific antibody delivery platform of claim 1, wherein an average particle size of the protein-type nanoparticle is within a range of 100 nm to 200 nm.

9. The multi-specific antibody delivery platform of claim 1, wherein the multi-specific antibody delivery platform delivers at least two specific antibodies.

10. A mufti-specific antibody delivery system, comprising the multi-specific antibody delivery platform of claim 1 and a specific antibody.

* * * * *